US008609343B2

(12) United States Patent
Chung et al.

(10) Patent No.: US 8,609,343 B2
(45) Date of Patent: Dec. 17, 2013

(54) DETECTION OF BLADDER CANCER

(75) Inventors: Woonbok Chung, Haverford, PA (US); Bogdan A. Czerniak, Houston, TX (US); Jean-Pierre Issa, Philadelphia, PA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/417,642

(22) Filed: Mar. 12, 2012

(65) Prior Publication Data

US 2012/0230952 A1    Sep. 13, 2012

Related U.S. Application Data

(60) Provisional application No. 61/451,744, filed on Mar. 11, 2011.

(51) Int. Cl.
*A61B 5/20* (2006.01)

(52) U.S. Cl.
USPC ........................................ 435/6.14; 435/6.11

(58) Field of Classification Search
None
See application file for complete search history.

(56) References Cited

U.S. PATENT DOCUMENTS

2007/0237770 A1* 10/2007 Lai et al. ..................... 424/138.1
2009/0011950 A1*  1/2009 Inazawa et al. .................. 506/9
2010/0304992 A1   12/2010 An et al.

FOREIGN PATENT DOCUMENTS

WO    WO 2009/069984    6/2009

OTHER PUBLICATIONS

J Cancer Res Clin Oncol. Jul. 2004;130(7):367-74. Immunotherapy of cancer: from vision to standard clinical practice. Huber CH, Wölfel T.*
Reduced representation bisulfite sequencing for comparative high-resolution DNA methylation analysis. Meissner A, Gnirke A, Bell GW, Ramsahoye B, Lander ES, Jaenisch R. Nucleic Acids Res. Oct. 13, 2005;33(18):5868-77. Print 2005.*
Interest of methylated genes as biomarkers in urothelial cell carcinomas of the urinary tract. Phé V, Cussenot O, Rouprêt M. BJU Int. Oct. 2009;104(7):896-901. Epub Jun. 12, 2009. Review.*
Diagnosis and treatment of bladder cancer. Sharma S, Ksheersagar P, Sharma P. Am Fam Physician. Oct. 1, 2009;80(7):717-23. Review.*
Biomarker Discovery and Application in Bladder Cancer Clinical Trial identifier: NCT00962052 (on ClinicalTrials.gov) Wolfson Medical Center.*
Epigenomics. Oct. 2009;1(1):99-110. Epigenetic biomarker development. Bock C.*
Variable DNA methylation patterns associated with progression of disease in hepatocellular carcinomas. Gao W, Kondo Y, Shen L, Shimizu Y, Sano T, Yamao K, Natsume A, Goto Y, Ito M, Murakami H, Osada H, Zhang J, Issa JP, Sekido Y. Carcinogenesis. Oct. 2008;29(10):1901-10. Epub Jul. 16, 2008.*
Mamm Genome. Feb. 2001;12(2):157-62. Cloning, expression and chromosomal location of NKX6B to 10Q26, a region frequently deleted in brain tumors. Lee SH, Davison JA, Vidal SM, Belouchi A.*
Structure and methylation-based silencing of a gene (DBCCR1) within a candidate bladder cancer tumor suppressor region at 9q32-q33. Habuchi T, Luscombe M, Elder PA, Knowles MA. Genomics. Mar. 15, 1998;48(3):277-88.*
Detection of bladder tumor by quantitative methylation specific real time PCR from urine sediment DNA American Association for Cancer Research Poster Location: Exhibit Hall A-C, Poster Section 3 Poster Board No. 18 Woonbok Chung, Jolanta Bondaruk, Daniel D. Kim, Bogdan Czerniak, Jean-Pierre J. Issa.*
Henk Merkus Particle Size Measurements: Fundamentals, Practice Quality Springer Science+Business Media B.V. 2009.*
Allard et al., "The early clinical course of primary Ta and T1 bladder cancer: a proposed prognostic index," *Br. J. Urol.*, 81:692-698, 1998.
Babjuk et al., "EAU guidelines on non-muscle-invasive urothelial carcinoma of the bladder." *Eur. Urol.*, 54:303-314, 2008.
Belinsky et al., "Aberrant methylation of p16(INK4a) is an early event in lung cancer and a potential biomarker for early diagnosis," *Proc Natl Acad Sci USA*, 95:11891-11896, 1998.
Belinsky, "Gene-promoter hypermethylation as a biomarker in lung cancer," *Nat Rev Cancer*, 4:707-717, 2004.
Bock et al., "Quantitative comparison of genome-wide DNA methylation mapping technologies," *Nat. Biotechnol.*, 28(10):1106-1114, 2010.
Brawer et al., "Complexed prostate specific antigen provides significant enhancement of specificity compared with total prostate specific antigen for detecting prostate cancer," *J. Urol.*, 163:1476-1480, 2000.
Brown et al., "Screening mammography in community practice: positive predictive value of abnormal findings and yield of follow-up diagnostic procedures," *Am J. Roentgenol.*, 165:1373-1377, 1995.
Cappellen et al., "Frequent loss of heterozygosity on chromosome 10q in muscle-invasive transitional cell carcinomas of the bladder," *Oncogene*, 14(25):3059-3066, 1997.
Catalona et al., "Measurement of prostate-specific antigen in serum as a screening test for prostate cancer," *N. Engl. J. Med.*, 324:1156-1161, 1991.
Chan et al., "Hypermethylation of multiple genes in tumor tissues and voided urine in urinary bladder cancer patients," *Clin Cancer Res.*, 8:464-470, 2002.
Chernova et al., "A novel member of the WD-repeat gene family, WDR11, maps to the 10q26 region and is disrupted by a chromosome translocation in human glioblastoma cells," *Oncogene*; 20(38):5378-5392, 2001.
Chung et al., "Detection of bladder tumor by quantitative methylation specific real time PCR from urine sediment DNA," Abstract, *American Association for Cancer Research*, Apr. 2010.
Chung et al, "Identification of novel tumor markers in prostate, colon and breast cancer by unbiased methylation profiling," *PLoS One*, 3:e2079, 2008.

(Continued)

*Primary Examiner* — Brian J Gangle
*Assistant Examiner* — Andrea McCollum
(74) *Attorney, Agent, or Firm* — Parker Highlander PLLC

(57) ABSTRACT

Provided are methods for detecting bladder cancer in a subject. In some aspects, methylation of one or more of MYO3A, CA10, NKX6-2, SOX11, DBC1, NPTX2, and/or A2BP1 in DNA sediment from a urine sample may be evaluated to detect the presence or absence of a bladder cancer in a human patient.

22 Claims, 5 Drawing Sheets

(56) References Cited

OTHER PUBLICATIONS

Denzinger et al., "Clinically relevant reduction in risk of recurrence of superficial bladder cancer using 5-aminolevulinic acid-induced fluorescence diagnosis: 8-year results of prospective randomized study," *Urology*, 69:675-679, 2007.
Diehl et al., "BEAMing: single-molecule PCR on microparticles in water-in-oil emulsions," *Nat. Methods*, 3(7):551-559, 2006.
Dulaimi et al., "Detection of bladder cancer in urine by a tumor suppressor gene hypermethylation panel," *Clin Cancer Res*, 10:1887-1893, 2004.
Eads et al., "MethyLight: a high-throughput assay to measure DNA methylation," *Nucleic Acids Res.*, 28(8):E32, 2000.
Estecio et al., "High-throughput methylation profiling by MCA coupled to CpG island microarray," *Genome Res.*, 17:1529-1536, 2007.
Feng et al., "Fluorescent conjugated polymer-based FRET technique for detection of DNA methylation of cancer cells," *Nat. Protoc.*, 5(7):1255-1264, 2010.
Friedrich et al., "Detection of methylated apoptosis-associated genes in urine sediments of bladder cancer patients," *Clin Cancer Res*, 10:7457-7465, 2004.
Gazdar and Czerniak, "Filling the void: urinary markers for bladder cancer risk and diagnosis," *J. Natl. Cancer Inst.*, 93:413-415, 2001.
Goo et al., "Stromal mesenchyme cell genes of the human prostate and bladder," *BMC Urol*, 5:17, 2005.
Grossman et al., "Detection of bladder cancer using a point-of-care proteomic assay," *JAMA*, 293:810-816, 2005.
Gustavsson et al., "SOX11 expression correlates to promoter methylation and regulates tumor growth in hematopoietic malignancies," *Mol Cancer*, 9(1):187, 2010.
Habuchi et al., "Hypermethylation at 9q32-33 tumour suppressor region is age-related in normal urothelium and an early and frequent alteration in bladder cancer," *Oncogene*, 20(4):531-7, 2001.
Habuchi et al., "Structure and methylation-based silencing of a gene (DBCCR1) within a candidate bladder cancer tumor suppressor region at 9q32-q33," *Genomics*, 48(3):277-288, 1998.
Hajdinjak, "UroVysion FISH test for detecting urothelial cancers: meta-analysis of diagnostic accuracy and comparison with urinary cytology testing," *Urol. Oncol.*, 26:646-651, 2008.
Hoffman et al., "Prostate-specific antigen testing accuracy in community practice," *BMC Fam. Pract.*, 3:19, 2002.
Hogue et al., "Quantitation of promoter methylation of multiple genes in urine DNA and bladder cancer detection," *J Natl Cancer Inst.* 98:996-1004, 2006.
Hoque et al., "Quantitative detection of promoter hypermethylation of multiple genes in the tumor, urine, and serum DNA of patients with renal cancer," *Cancer Res*, 64:5511-5517, 2004.
Jemal et al., "Cancer statistics, 2009," *Cancer J. Clin.*, 59:225-249, 2009.
Jones and Baylin, "The fundamental role of epigenetic events in cancer," *Nat Rev Genet*, 3:415-428, 2002.
Kerlikowske et al., "Positive predictive value of screening mammography by age and family history of breast cancer," *JAMA*, 270:2444-2450, 1993.
Keshet et al., "Evidence for an instructive mechanism of de novo methylation in cancer cells," *Nat. Genet.*, 38(2):149-53, 2006.
Kriegmair et al., "Detection of early bladder cancer by 5-aminolevulinic acid induced porphyrin fluorescence." *J. Urol.*, 155:105-109, 1996.
Kristensen et al., "Sensitive Melting Analysis after Real Time-Methylation Specific PCR (Smart-MSP): high-throughput and probe-free quantitative DNA methylation detection," *Nucleic Acids Res.*, 36(7):e42, 2008.
Kurth et al., "Factors affecting recurrence and progression in superficial bladder tumours," *Eur. J. Cancer*, 31A:1840-1846, 1995.
Li et al., "Sensitive digital quantification of DNA methylation in clinical samples," *Nat. Biotechnol.*, 27(9):858-863, 2009.
Lotan and Roehrborn, "Sensitivity and specificity of commonly available bladder tumor markers versus cytology: results of a comprehensive literature review and meta-analyses," *Urology*, 61:109-118, 2003.
Mandel et al., "The effect of fecal occult-blood screening on the incidence of colorectal cancer," *N. Engl. J. Med.*, 343:1603-1607, 2000.
Meissner et al., "Reduced representation bisulfite sequencing for comparative high-resolution DNA methylation analysis," *Nucleic Acids Res.*, 33(18):5868-5877, 2005.
Richie et al., "Effect of patient age on early detection of prostate cancer with serum prostate-specific antigen and digital rectal examination," *Urology*, 42:365-374, 1993.
Shen et al., "Genome-wide profiling of DNA methylation reveals a class of normally methylated CpG island promoters," *PLoS Genet*, 3:2023-2036, 2007.
Smith et al., "High-throughput bisulfite sequencing in mammalian genomes," *Methods*, 48(3):226-232, 2009.
Sul et al., "Identification of aberrant promoter methylation of THX5, PENK and T in detection of urothelial carcinoma in exfoliated urine cells," *Urology*, 72 (Supplement 5A), Abstract MP-2.10, 2008.
Sylvester et al., "Predicting recurrence and progression in individual patients with stage Ta T1 bladder cancer using EORTC risk tables: a combined analysis of 2596 patients from seven EORTC trials," *Eur. Urol.*, 49:466-477, 2006.
Tong et al., "Genome-wide DNA methylation profiling of chronic lymphocytic leukemia allows identification of epigenetically repressed molecular pathways with clinical impact," *Epigenetics*, 5(6), 2010.
Ueki et al., "Identification and characterization of differentially methylated CpG islands in pancreatic carcinoma," *Cancer Res*, 61(23):8540-8546, 2001.
van Rhijn et al., "Urine markers for bladder cancer surveillance: a systematic review," *Eur. Urol.*, 47:736-748, 2005.
Venkatesan et al., "Positive predictive value of specific mammographic findings according to reader and patient variables," *Radiology*, 250:648-657, 2009.
Watanabe et al., "Sensitive and specific detection of early gastric cancer with DNA methylation analysis of gastric washes," *Gastroenterology*, 136:2149-2158, 2009.
Weisenberger et al., "DNA methylation analysis by digital bisulfite genomic sequencing and digital MethyLight," *Nucleic Acids Res.*, 36:4689-4698, 2008.
Wong et al. "Rapid and quantitative method of allele-specific DNA methylation analysis," *BioTechniques*, 41(6);734-9, 2006.
Yu et al., "A novel set of DNA methylation markers in urine sediments for sensitive/specific detection of bladder cancer," *Clin Cancer Res*, 13:7296-7304, 2007.
Zaak et al., "Endoscopic detection of transitional cell carcinoma with 5-aminolevulinic acid: results of 1012 fluorescence endoscopies," *Urology*, 57:690-694, 2001.

\* cited by examiner

FIGS. 3A-D

FIGS. 5A-B
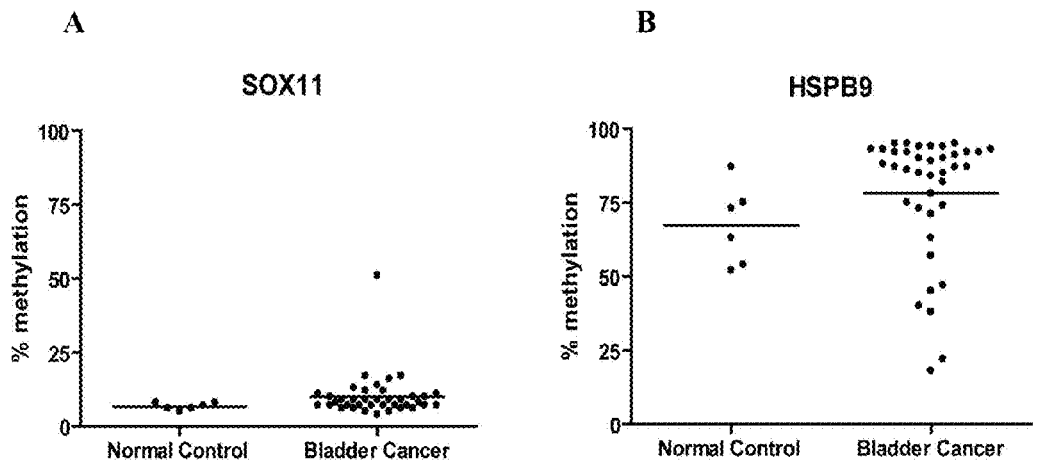
FIGS. 6A-B
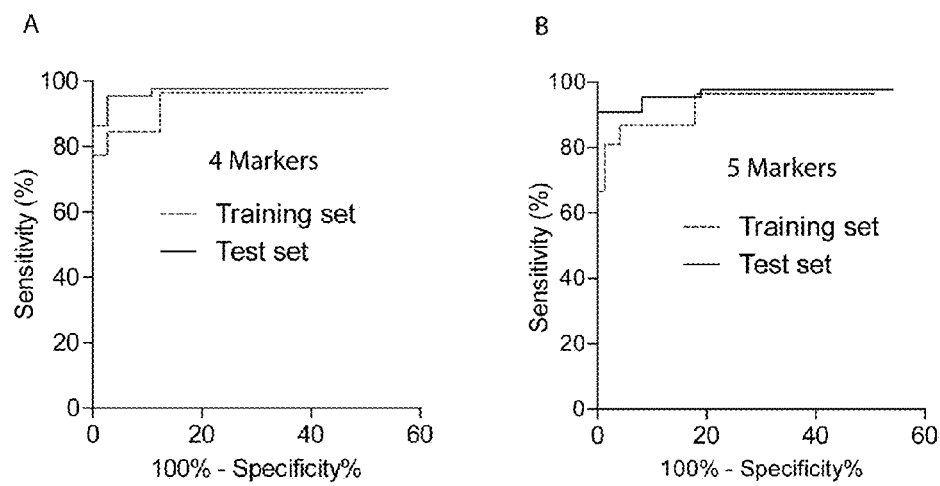

SEQUENCE LISTING

<160> NUMBER OF SEQ ID NOS: 88

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1

-continued

```
ttttagaggg gagggtaggg gtagt                                          25

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
tccactccat taacccaaat caa                                            23

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
ggggtagtag agtaggggaa gaat                                           24

<210> SEQ ID NO 4
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 4
utccactcca ttaacccaaa tcaa                                           24

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
agaattgggt agtttgtaga                                                20

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
agttggggga gtgatgttat tta                                            23

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
aacaacccca aaccccctctc t                                             21

<210> SEQ ID NO 8
```

```
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
gggggagtga tgttatttat atgat                                              25

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9 accccccaact ctcccaaac                                                    19

<210> SEQ ID NO 10
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 10 uccccccaact ctcccaaac                                                    19

<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
gagattttaa tttttgtag aag                                                 23

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
tggagaatgg agagggaagt tt                                                 22

<210> SEQ ID NO 13
<211> LENGTH: 19
<212> TYPE: DNA
<213> ORGANISM: Artificial Sequence
<220> FEATURE:
<223> OTHER INFORMATION: Synthetic primer

<400> SEQUENCE: 13
cccctccccc attcatttt                                                     19

<210> SEQ ID NO 14
<211> LENGTH: 20
<212> TYPE: DNA
<213> ORGANISM: Artificial Sequence
<220> FEATURE:
<223> OTHER INFORMATION: Synthetic primer
```

```
<220> FEATURE:
<221> NAME/KEY: misc_feature
<223> OTHER INFORMATION: This is combined RNA/DNA sequence

<400> SEQUENCE: 14
uccccucccc cattcatttt                                                      20

<210> SEQ ID NO 15
<211> LENGTH: 18
<212> TYPE: DNA
<213> ORGANISM: Artificial Sequence
<220> FEATURE:
<223> OTHER INFORMATION: Synthetic primer

<400> SEQUENCE: 15
tggagaggga agtttaag                                                        18

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
ggggattgga aaggaggtga                                                      20

<210> SEQ ID NO 17
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
ctccccccct cctacaaa                                                        18

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
ccccaacccc cttcctaa                                                        18

<210> SEQ ID NO 19
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 19
uccccaaccc ccttcctaa                                                       19

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
```
aaggaggtga tttttaaatt                                               20

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
gggttttgaa gagaaggttt a                                             21

<210> SEQ ID NO 22
<211> LENGTH: 27
<212> TYPE: DNA
<213> ORGANISM: Artificial Sequence
<220> FEATURE:
<223> OTHER INFORMATION: Synthetic primer

<400> SEQUENCE: 22
tacccctttc tcaaataac ttctaac                                        27

<210> SEQ ID NO 23
<211> LENGTH: 19
<212> TYPE: DNA
<213> ORGANISM: Artificial Sequence
<220> FEATURE:
<223> OTHER INFORMATION: Synthetic primer

<400> SEQUENCE: 23
tccaaccccc actaccatc                                                19

<210> SEQ ID NO 24
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 24
utccaacccc cactaccatc                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
ggttttgaag agaaggttta                                               20

<210> SEQ ID NO 26
<211> LENGTH: 24
<212> TYPE: DNA
<213> ORGANISM: Artificial Sequence
<220> FEATURE:
<223> OTHER INFORMATION: Synthetic primer

<400> SEQUENCE: 26
ggaaaagagt agggtgtttt aggt                                          24

<210> SEQ ID NO 27

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 27
cccccaaaaa tactcctttc t                                              21

<210> SEQ ID NO 28
<211> LENGTH: 19
<212> TYPE: DNA
<213> ORGANISM: Artificial Sequence
<220> FEATURE:
<223> OTHER INFORMATION: Synthetic primer

<400> SEQUENCE: 28
ccccacccac aacttttaa                                                 19

<210> SEQ ID NO 29
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 29
uccccaccca caacttttaa                                                20

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
gagtagggtg ttttaggtag t                                              21

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
gggacaccgc tgatcgttta                                                20

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
ttgtatgtat gtgagtgtgg gaga                                           24

<210> SEQ ID NO 33
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 33
tttcttccac cccttctctt c                                              21

<210> SEQ ID NO 34
<211> LENGTH: 18
<212> TYPE: DNA
<213> ORGANISM: Artificial Sequence
<220> FEATURE:
<223> OTHER INFORMATION: Synthetic primer

<400> SEQUENCE: 34
ctccccctct aactctat                                                  18

<210> SEQ ID NO 35
<211> LENGTH: 18
<212> TYPE: DNA
<213> ORGANISM: Artificial Sequence
<220> FEATURE:
<223> OTHER INFORMATION: Synthetic primer

<400> SEQUENCE: 35
tcggcgggag gatttgat                                                  18

<210> SEQ ID NO 36
<211> LENGTH: 19
<212> TYPE: DNA
<213> ORGANISM: Artificial Sequence
<220> FEATURE:
<223> OTHER INFORMATION: Synthetic primer

<400> SEQUENCE: 36
cccgcgaacc gaaataaaa                                                 19

<210> SEQ ID NO 37
<211> LENGTH: 18
<212> TYPE: DNA
<213> ORGANISM: Artificial Sequence
<220> FEATURE:
<223> OTHER INFORMATION: Synthetic primer

<400> SEQUENCE: 37
tgggttaatc gagtcgaa                                                  18

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
ttcggcgttt tggacgtatt                                                20

<210> SEQ ID NO 39
<211> LENGTH: 17
<212> TYPE: DNA
<213> ORGANISM: Artificial Sequence
<220> FEATURE:
<223> OTHER INFORMATION: Synthetic primer

<400> SEQUENCE: 39
aatccgcgcg caaccta                                                   17

<210> SEQ ID NO 40
<211> LENGTH: 19
```

```
<212> TYPE: DNA
<213> ORGANISM: Artificial Sequence
<220> FEATURE:
<223> OTHER INFORMATION: Synthetic primer

<400> SEQUENCE: 40
tcggaattcg gttgagagg                                                    19

<210> SEQ ID NO 41
<211> LENGTH: 24
<212> TYPE: DNA
<213> ORGANISM: Artificial Sequence
<220> FEATURE:
<223> OTHER INFORMATION: Synthetic primer

<400> SEQUENCE: 41
ggtaggagtt acgagtcgga gaga                                              24

<210> SEQ ID NO 42
<211> LENGTH: 23
<212> TYPE: DNA
<213> ORGANISM: Artificial Sequence
<220> FEATURE:
<223> OTHER INFORMATION: Synthetic primer

<400> SEQUENCE: 42
actacgatcg cgacaaaaaa aac                                               23

<210> SEQ ID NO 43
<211> LENGTH: 17
<212> TYPE: DNA
<213> ORGANISM: Artificial Sequence
<220> FEATURE:
<223> OTHER INFORMATION: Synthetic primer

<400> SEQUENCE: 43
tcgggttgtt tcgatcg                                                      17

<210> SEQ ID NO 44
<211> LENGTH: 19
<212> TYPE: DNA
<213> ORGANISM: Artificial Sequence
<220> FEATURE:
<223> OTHER INFORMATION: Synthetic primer

<400> SEQUENCE: 44
cgcgttattt cgggaatcg                                                    19

<210> SEQ ID NO 45
<211> LENGTH: 25
<212> TYPE: DNA
<213> ORGANISM: Artificial Sequence
<220> FEATURE:
<223> OTHER INFORMATION: Synthetic primer

<400> SEQUENCE: 45
tcccgaccga caacttttaa ataaa                                             25

<210> SEQ ID NO 46
<211> LENGTH: 17
<212> TYPE: DNA
<213> ORGANISM: Artificial Sequence
<220> FEATURE:
<223> OTHER INFORMATION: Synthetic primer

<400> SEQUENCE: 46
aggcgatttg agtcgtt                                                      17
```

<210> SEQ ID NO 47
<211> LENGTH: 22
<212> TYPE: DNA
<213> ORGANISM: Artificial Sequence
<220> FEATURE:
<223> OTHER INFORMATION: Synthetic primer

<400> SEQUENCE: 47
ggcggcgttt atggatatta at                                           22

<210> SEQ ID NO 48
<211> LENGTH: 22
<212> TYPE: DNA
<213> ORGANISM: Artificial Sequence
<220> FEATURE:
<223> OTHER INFORMATION: Synthetic primer

<400> SEQUENCE: 48
gcgaccaacg aaacactact ca                                           22

<210> SEQ ID NO 49
<211> LENGTH: 13
<212> TYPE: DNA
<213> ORGANISM: Artificial Sequence
<220> FEATURE:
<223> OTHER INFORMATION: Synthetic primer

<400> SEQUENCE: 49
ttcgggcgcg ttc                                                     13

<210> SEQ ID NO 50
<211> LENGTH: 23
<212> TYPE: DNA
<213> ORGANISM: Artificial Sequence
<220> FEATURE:
<223> OTHER INFORMATION: Synthetic primer

<400> SEQUENCE: 50
cgtgtagggt gttgtgttta tgc                                          23

<210> SEQ ID NO 51
<211> LENGTH: 23
<212> TYPE: DNA
<213> ORGANISM: Artificial Sequence
<220> FEATURE:
<223> OTHER INFORMATION: Synthetic primer

<400> SEQUENCE: 51
aacaccaaaa ttccgaattt acg                                          23

<210> SEQ ID NO 52
<211> LENGTH: 21
<212> TYPE: DNA
<213> ORGANISM: Artificial Sequence
<220> FEATURE:
<223> OTHER INFORMATION: Synthetic primer

<400> SEQUENCE: 52
atttaaaggg atcgcgtata c                                            21

<210> SEQ ID NO 53
<211> LENGTH: 17
<212> TYPE: DNA
<213> ORGANISM: Artificial Sequence
<220> FEATURE:
<223> OTHER INFORMATION: Synthetic primer

```
<400> SEQUENCE: 53
tgagggcggc ggtaaac                                                    17

<210> SEQ ID NO 54
<211> LENGTH: 21
<212> TYPE: DNA
<213> ORGANISM: Artificial Sequence
<220> FEATURE:
<223> OTHER INFORMATION: Synthetic primer

<400> SEQUENCE: 54
cccgataccc ctttctcaaa a                                               21

<210> SEQ ID NO 55
<211> LENGTH: 16
<212> TYPE: DNA
<213> ORGANISM: Artificial Sequence
<220> FEATURE:
<223> OTHER INFORMATION: Synthetic primer

<400> SEQUENCE: 55
tgtcgcgtta gaagtt                                                     16

<210> SEQ ID NO 56
<211> LENGTH: 22
<212> TYPE: DNA
<213> ORGANISM: Artificial Sequence
<220> FEATURE:
<223> OTHER INFORMATION: Synthetic primer

<400> SEQUENCE: 56
ggtttcgttc gtcgttcgtt at                                              22

<210> SEQ ID NO 57
<211> LENGTH: 20
<212> TYPE: DNA
<213> ORGANISM: Artificial Sequence
<220> FEATURE:
<223> OTHER INFORMATION: Synthetic primer

<400> SEQUENCE: 57
cctcctccaa ccaaaatcga                                                 20

<210> SEQ ID NO 58
<211> LENGTH: 18
<212> TYPE: DNA
<213> ORGANISM: Artificial Sequence
<220> FEATURE:
<223> OTHER INFORMATION: Synthetic primer

<400> SEQUENCE: 58
ttcgcgttgt ttggagaa                                                   18

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
gaggggttag gatgggagtt                                                 20

<210> SEQ ID NO 60
<211> LENGTH: 25
```

```
<212> TYPE: DNA
<213> ORGANISM: Artificial Sequence
<220> FEATURE:
<223> OTHER INFORMATION: Synthetic primer

<400> SEQUENCE: 60
ctcttcatct ccaccatatt ataca                                           25

<210> SEQ ID NO 61
<211> LENGTH: 22
<212> TYPE: DNA
<213> ORGANISM: Artificial Sequence
<220> FEATURE:
<223> OTHER INFORMATION: Synthetic primer

<400> SEQUENCE: 61
ccaccaacca aacactactc aa                                              22

<210> SEQ ID NO 62
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 62
uccaccaacc aaacactact caa                                             23

<210> SEQ ID NO 63
<211> LENGTH: 19
<212> TYPE: DNA
<213> ORGANISM: Artificial Sequence
<220> FEATURE:
<223> OTHER INFORMATION: Synthetic primer

<400> SEQUENCE: 63
ggaggagttt atggatatt                                                  19

<210> SEQ ID NO 64
<211> LENGTH: 22
<212> TYPE: DNA
<213> ORGANISM: Artificial Sequence
<220> FEATURE:
<223> OTHER INFORMATION: Synthetic primer

<400> SEQUENCE: 64
tattaaagaa ggtggggaag gg                                              22

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
tcaaccaccc ccatcttacc                                                 20

<210> SEQ ID NO 66
<211> LENGTH: 23
<212> TYPE: DNA
<213> ORGANISM: Artificial Sequence
<220> FEATURE:
<223> OTHER INFORMATION: Synthetic primer
```

-continued

```
<400> SEQUENCE: 66
ggtaggagtt tgggaggaga gta                                          23

<210> SEQ ID NO 67
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 67
utcaaccacc cccatcttac c                                            21

<210> SEQ ID NO 68
<211> LENGTH: 18
<212> TYPE: DNA
<213> ORGANISM: Artificial Sequence
<220> FEATURE:
<223> OTHER INFORMATION: Synthetic primer

<400> SEQUENCE: 68
gagtttggga ggagagta                                                18

<210> SEQ ID NO 69
<211> LENGTH: 29
<212> TYPE: DNA
<213> ORGANISM: Artificial Sequence
<220> FEATURE:
<223> OTHER INFORMATION: Synthetic primer

<400> SEQUENCE: 69
gatttggtga agtaggtttt aagtttagg                                    29

<210> SEQ ID NO 70
<211> LENGTH: 24
<212> TYPE: DNA
<213> ORGANISM: Artificial Sequence
<220> FEATURE:
<223> OTHER INFORMATION: Synthetic primer

<400> SEQUENCE: 70
tccaccaatc tctcccttta ctct                                         24

<210> SEQ ID NO 71
<211> LENGTH: 28
<212> TYPE: DNA
<213> ORGANISM: Artificial Sequence
<220> FEATURE:
<223> OTHER INFORMATION: Synthetic primer

<400> SEQUENCE: 71
gaagtaggtt ttaagtttag gaggtttg                                     28

<210> SEQ ID NO 72
<211> LENGTH: 25
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 72
```
utccaccaat ctctcccttt actct                                    25

<210> SEQ ID NO 73
<211> LENGTH: 20
<212> TYPE: DNA
<213> ORGANISM: Artificial Sequence
<220> FEATURE:
<223> OTHER INFORMATION: Synthetic primer

<400> SEQUENCE: 73
taggttttaa gtttaggagg                                          20

<210> SEQ ID NO 74
<211> LENGTH: 33
<212> TYPE: DNA
<213> ORGANISM: Artificial Sequence
<220> FEATURE:
<223> OTHER INFORMATION: Synthetic primer

<400> SEQUENCE: 74
taggagagga aataaagatt tttgtagttg tat                           33

<210> SEQ ID NO 75
<211> LENGTH: 25
<212> TYPE: DNA
<213> ORGANISM: Artificial Sequence
<220> FEATURE:
<223> OTHER INFORMATION: Synthetic primer

<400> SEQUENCE: 75
ctattttcct aaactcccca aaacc                                    25

<210> SEQ ID NO 76
<211> LENGTH: 24
<212> TYPE: DNA
<213> ORGANISM: Artificial Sequence
<220> FEATURE:
<223> OTHER INFORMATION: Synthetic primer

<400> SEQUENCE: 76 aaaccccaa ttacctaact tcca                                      24

<210> SEQ ID NO 77
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: This is combined RNA/DNA sequence

<400> SEQUENCE: 77 uaaccccaa ttacctaact tcca                                      24

<210> SEQ ID NO 78
<211> LENGTH: 20
<212> TYPE: DNA
<213> ORGANISM: Artificial Sequence
<220> FEATURE:
<223> OTHER INFORMATION: Synthetic primer

<400> SEQUENCE: 78
gtagttgtat tgaggaaaat                                          20

<210> SEQ ID NO 79
<211> LENGTH: 17

```
<212> TYPE: DNA
<213> ORGANISM: Artificial Sequence
<220> FEATURE:
<223> OTHER INFORMATION: Synthetic primer

<400> SEQUENCE: 79
gggygggtyg aaggtyg                                                    17

<210> SEQ ID NO 80
<211> LENGTH: 11
<212> TYPE: DNA
<213> ORGANISM: Artificial Sequence
<220> FEATURE:
<223> OTHER INFORMATION: Synthetic primer

<400> SEQUENCE: 80
gagygygygy g                                                          11

<210> SEQ ID NO 81
<211> LENGTH: 9
<212> TYPE: DNA
<213> ORGANISM: Artificial Sequence
<220> FEATURE:
<223> OTHER INFORMATION: Synthetic primer

<400> SEQUENCE: 81 tgygtygyg                                                              9

<210> SEQ ID NO 82
<211> LENGTH: 9
<212> TYPE: DNA
<213> ORGANISM: Artificial Sequence
<220> FEATURE:
<223> OTHER INFORMATION: Synthetic primer

<400> SEQUENCE: 82 tygygttyg                                                              9

<210> SEQ ID NO 83
<211> LENGTH: 11
<212> TYPE: DNA
<213> ORGANISM: Artificial Sequence
<220> FEATURE:
<223> OTHER INFORMATION: Synthetic primer

<400> SEQUENCE: 83
ygtttgtygy g                                                          11

<210> SEQ ID NO 84
<211> LENGTH: 15
<212> TYPE: DNA
<213> ORGANISM: Artificial Sequence
<220> FEATURE:
<223> OTHER INFORMATION: Synthetic primer

<400> SEQUENCE: 84
ttygygttgg gggyg                                                      15

<210> SEQ ID NO 85
<211> LENGTH: 13
<212> TYPE: DNA
<213> ORGANISM: Artificial Sequence
<220> FEATURE:
<223> OTHER INFORMATION: Synthetic primer

<400> SEQUENCE: 85
ttygatagyg gyg                                                        13
```

```
<210> SEQ ID NO 86
<211> LENGTH: 15
<212> TYPE: DNA
<213> ORGANISM: Artificial Sequence
<220> FEATURE:
<223> OTHER INFORMATION: Synthetic primer

<400> SEQUENCE: 86
aatygttygg gygyg                                                      15

<210> SEQ ID NO 87
<211> LENGTH: 12
<212> TYPE: DNA
<213> ORGANISM: Artificial Sequence
<220> FEATURE:
<223> OTHER INFORMATION: Synthetic primer

<400> SEQUENCE: 87
gttgygggyg yg                                                         12

<210> SEQ ID NO 88
<211> LENGTH: 13
<212> TYPE: DNA
<213> ORGANISM: Artificial Sequence
<220> FEATURE:
<223> OTHER INFORMATION: Synthetic primer

<400> SEQUENCE: 88
tttgttttyg tyg                                                        13
```

US 8,609,343 B2

DETECTION OF BLADDER CANCER

This application claims priority to U.S. Application No. 61/451,744 filed on Mar. 11, 2011, the entire disclosure of which is specifically incorporated herein by reference in its entirety without disclaimer.

This invention was made with government support under U01 CA 85078, 1R01 CA151489, P50 CA 91846, and CA16672 awarded by the National Institutes of Health. The government has certain rights in the invention.

BACKGROUND OF THE INVENTION

1. Field of the Invention

The present invention relates generally to the fields of molecular biology and medicine. More particularly, it concerns the proteomic diagnosis, classification and grading of bladder cancer based on the presence or absence of methylation in certain genes.

2. Description of Related Art

Bladder cancer is the fifth most common cancer in the United States and causes approximately 3% of all cancer-related deaths (Jemal et al., 2009). More than 90% of bladder cancers are derived from the transitional epithelium and are thus called transitional cell carcinoma (TCC). Most (75-85%) bladder cancers are non-muscle invasive tumors (pTa, Tis and pT1) at first diagnosis (Babjuk et al., 2008). Generally, the prognosis of non-invasive tumors is good, although up to 80% of cases will recur after complete transurethral resection and up to 45% of cases will progress to invasive cancer in 5 years (Babjuk et al., 2008; Kurth et al., 1995; Allard et al., 1998; Sylvester et al., 2006).

Significant costs and limitations are associated with current methods for the detection of bladder cancer. Currently, diagnosis of bladder cancer typically involves urinary cytology in combination with cystoscopy, including biopsy of suspicious lesions. Unfortunately, cystoscopy can miss 10% to 30% of malignancies and the procedure is invasive and uncomfortable (Kriegmair et al., 1996; Denzinger et al., 2007; Zaak et al., 2001). Voided urine cytology is the most common noninvasive method for detecting bladder tumors in symptomatic patients and population screening (Papanicolaou and Marshall, 1945) and has been reported to have 34-35% median sensitivity and 94-99% median specificity by meta-analyses (Lotan and Roehrborn, 2003; van Rhijn et al., 2005). Significant costs are also associated with urinary cystoscopy and urinary cytology. Clearly, there is a need for new methods for the diagnosis of bladder cancer.

SUMMARY OF THE INVENTION

The present invention overcomes limitations in the prior art by providing new methods for the detection of bladder cancer. In some aspects, these methods involve testing urine sediment DNA for the presence of methylation in one or more or all of a group of genes (e.g., MYO3A, CA10, NKX6-2, DBC1, PENK, NPTX2 and/or SOX11). Quantity of urine sediment DNA in one or more or all of these genes may also be used to detect bladder cancer in a subject, such as a human patient. In various embodiments and as shown in the below examples, the inventors have observed that quantifying methylated DNA, e.g., via quantitative methylation specific PCR (QMSP), for 4 genes (MYO3A, CA10, NKX6-2 and DBC1; or MYO3A, CA10, NKX6-2 and SOX11) can result in about 81% sensitivity and about 97% specificity, and testing 5 genes (MYO3A, CA10, NKX6-2, DBC1 and SOX11 or PENK) was observed to result in about 85% sensitivity and about 95% specificity for detection of bladder cancer.

DNA sediment from a biological sample may be tested to detect a cancer in a human subject. In certain embodiments where the subject is a human, the presence, amount or absence or methylation of one, two, three, four, five, six, seven, or all of DBC1 (Gene ID: 1620, "deleted in bladder cancer 1"), MYO3A (Gene ID: 53904, "myosin MA"), SOX11 (Gene ID: 6664, "SRY (sex determining region Y)-box 11"), NPTX2 (Gene ID: 4885, "neuronal pentraxin II"), NKX6-2 (Gene ID: 84504, "NK6 homeobox 2"), A2BP1 (Gene ID: ID: 54715, "RNA binding protein, fox-1 homolog (C. elegans) 1" or "RBFOX1"), PENK (Gene ID: 5179, "proenkephalin") and/or CA10 (Gene ID: 56934, "carbonic anhydrase X") genes may be measured. As would be appreciated by one of skill, variants of these genes also exist in other non-human mammals, and methods and/or kits may be altered to specifically identify one or more of these genes in a non-human mammal. The biological sample may comprise a urine sample, bladder cells, bladder tissue, urine sediment DNA, or DNA derived from urine sediment DNA. The methylation may be present in an intron, exon, promoter, CpG island, or CpG rich region of the gene(s).

An aspect of the present invention relates to a method of detecting the presence of, or an increased risk of, a bladder cancer in a subject, comprising detecting or measuring methylation in at least one of MYO3A, CA10, NKX6-2, SOX11, DBC1, NPTX2, and A2BP1 in a biological sample from the subject, wherein methylation in the at least one of MYO3A, CA10, NKX6-2, SOX11, DBC1, NPTX2, and A2BP1 indicates that the subject has, or has an increased risk of having, the bladder cancer. The method may further comprise measuring or detecting methylation in PENK in the biological sample, wherein methylation in PENK indicates that the subject has, or has an increased risk of having, the bladder cancer. The detecting or measuring may comprise detecting or measuring methylation in at least two, three, four, five, or all of MYO3A, CA10, NKX6-2, SOX11, DBC1, NPTX2. The detecting or measuring may comprise detecting or measuring methylation in MYO3A, CA10, and NKX6-2. The detecting may further comprise detecting or measuring methylation in SOX11 and/or PENK, wherein methylation in PENK indicates that the subject has, or has an increased risk of having, the bladder cancer. The detecting or measuring may comprise detecting or measuring methylation in at least four of MYO3A, CA10, NKX6-2, SOX11, DBC1. The detecting or measuring may comprise detecting or measuring methylation in MYO3A, CA10, NKX6-2, and DBC1. The detecting may further comprise detecting or measuring methylation in SOX11. The detecting may further comprises detecting or measuring methylation in PENK, wherein methylation in PENK indicates that the subject has, or has an increased risk of having, the bladder cancer. The detecting or measuring may comprise detecting or measuring methylation in MYO3A, SOX11, CA10, DBC1, PENK, and NKX6-2, wherein methylation in PENK indicates that the subject has, or has an increased risk of having, the bladder cancer. The subject may be a mammal, such as a human.

In some embodiments, the biological sample comprises a urine sample, bladder cells, bladder tissue, or DNA from or derived from urine sediment. The bladder cancer may comprises a papillary tumor and/or a non-papillary tumor. The method may further comprise a method of measuring the aggressiveness of the bladder cancer. In some embodiments, a personalized therapy is administered to the subject. The personalized therapy may be, e.g., a chemotherapeutic, an immunotherapy, a radiotherapy, or a surgery. The method may further comprise monitoring the effectiveness of a therapy that is administered to the subject. The detecting or measuring may comprise methylation specific PCR (MSP), real-time methylation specific PCR, methylation-sensitive single-strand conformation analysis (MS-SSCA), quantitative methylation specific PCR (QMSP), PCR using a methylated DNA-specific binding protein, high resolution melting analysis (HRM), methylation-sensitive single-nucleotide primer extension (MS-SnuPE), base-specific cleavage/MALDI-TOF, PCR, real-time PCR, Combined Bisulfite Restriction Analysis (COBRA), methylated DNA immunoprecipitation (MeDIP), a microarray-based method, pyrosequencing, reduced representation bisulfite sequencing (RRBS), methyl-BEAMing, FRET technique for detection of DNA methylation, or bisulfite sequencing. In some embodiments, the detecting or measuring comprises methylation specific PCR, real-time methylation specific PCR, quantitative methylation specific PCR (QMSP), or bisulfite sequencing.

Another aspect of the present invention relates to a kit comprising a sealed container comprising primers or probes designed to detect methylation in at least one, two, three, four, five, six, or seven genes selected from the group consisting of MYO3A, CA10, NKX6-2, SOX11, DBC1, NPTX2, and A2BP1. The kit may further comprise primers or probes designed to detect methylation in PENK. The kit may comprising primers or probes designed to detect methylation in each of MYO3A, CA10, NKX6-2, SOX11, DBC1, NPTX2, and A2BP1. The kit may further comprise one or more reagents for PCR, real-time PCR, or bisulfite sequencing.

Yet another aspect of the present invention relates to a biochip comprising an isolated nucleic acid comprising primers to detect methylation in at least one, two, three, four, five, six, or seven genes selected from the group consisting of MYO3A, CA10, NKX6-2, SOX11, DBC1, NPTX2, and A2BP1. The biochip may further comprise primers to detect methylation in PENK.

As used herein, "obtaining a biological sample" or "obtaining a urine sample" refer to receiving a biological or urine sample, e.g., either directly or indirectly. For example, in some embodiments, the biological sample (e.g., a urine sample) is directly obtained from a subject at or near the laboratory or location where the biological sample will be analyzed. In other embodiments, the biological sample may be drawn or taken by a third party and then transferred, e.g., to a separate entity or location for analysis. In other embodiments, the sample may be obtained and tested in the same location using a point-of care test. In these embodiments, said obtaining refers to receiving the sample, e.g., from the patient, from a laboratory, from a doctor's office, from the mail, courier, or post office, etc. In some further aspects, the method may further comprise reporting the determination to the subject, a health care payer, an attending clinician, a pharmacist, a pharmacy benefits manager, or any person that the determination may be of interest.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A, ROC curves of the biomarkers sets (2-5 markers) that showed the highest AUC. Detailed information of the best combined markers was summarized in Table 3. FIG. 3B, Detection of bladder cancer in urine sediments by stages. A case was determined positive for methylations of ≥3 markers were hypermethylated. FIG. 3C, AUC curves for the 5 marker set in muscle invasive and non-muscle invasive cancers. FIG. 3D, AUC curves for the 4 marker set in muscle invasive and non-muscle invasive cancers.

FIGS. 5A-B: Scatter plots of bisulfite pyrosequencing results for SOX11 (FIG. 5A) and HSPB9 (FIG. 5B) in urine sediments DNA from controls (n=6) and bladder cancer patients (n=38). Horizontal bars denote mean methylation levels for each group.

FIGS. 6A-B: Receiver operating characteristics (ROC) for detection of bladder cancer in urine sediments. The 128 urine samples from bladder tumor patients and 110 urine samples from control subjects were randomly divided into training set (tumor patients urine=84 and control urine=73) containing two third of samples and the rest of samples form a test set (tumor patients urine=44 and control urine=37). FIG. 6A, ROC for the model that includes methylation of 4 genes (MYO3A+CA10+NKX6-2+DBC1). The AUC is 0.929 (95% CI=0.874 to 0.962) for training set and 0.964 (95% CI=0.897 to 0.993) for the test set. FIG. 6B, ROC for the model that includes methylation of 5 genes (MYO3A+CA10+NKX6-2+DBC1+SOX11). The AUC is 0.929 (95% CI=0.877 to 0.964) for training set and 0.959 (95% CI=0.890 to 0.990) for the test set.

DESCRIPTION OF ILLUSTRATIVE EMBODIMENTS

Figure 1:
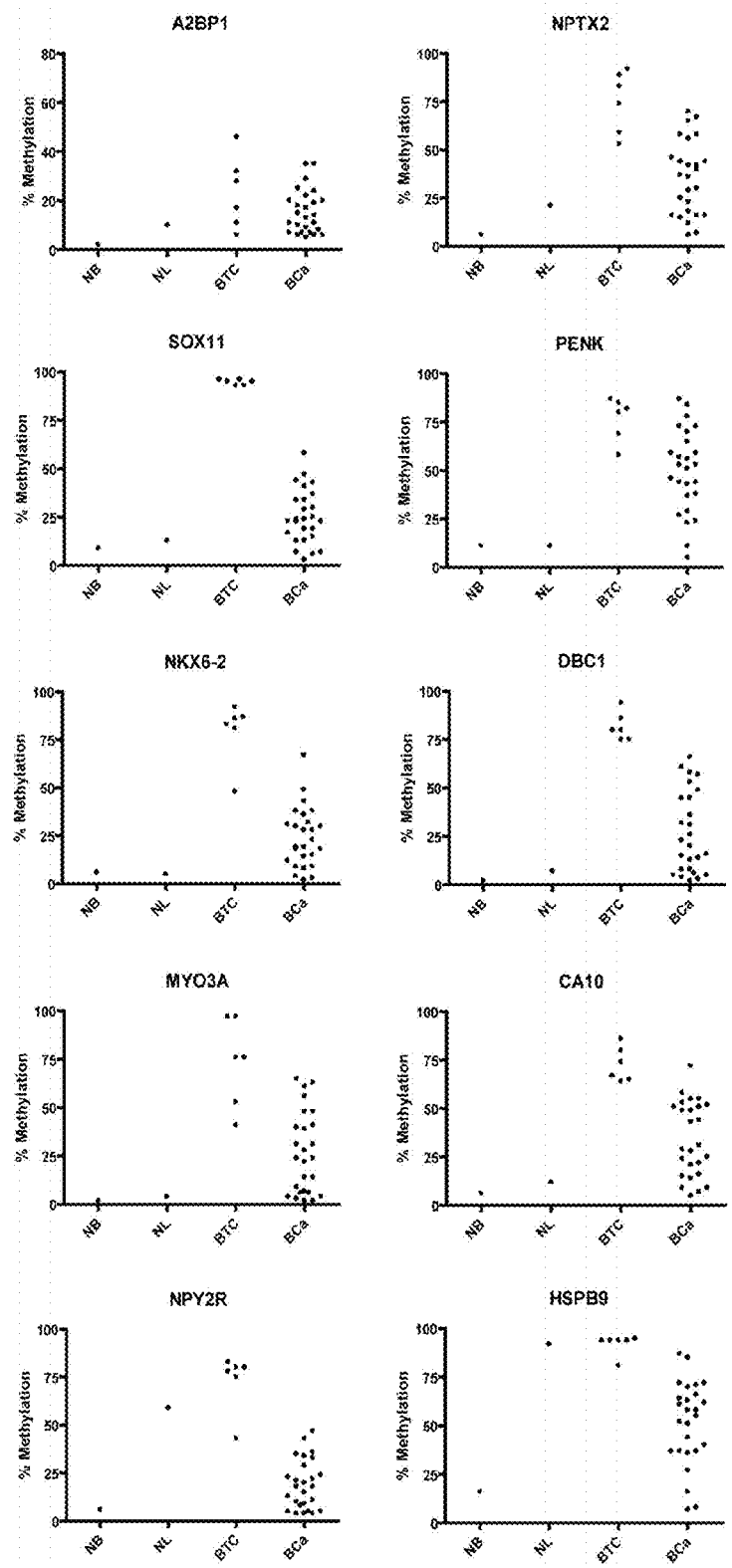
FIG. 1. Scatter plot of bisulfite pyrosequencing results of candidate genes in normal bladders (NB), normal leukocytes (NL), 6 bladder tumor cell lines (BTC) and 26 primary bladder tumors (BCa). We used a mixture of normal bladder DNA from 3 persons (2 males and 1 female) as a control (NB). We also analyzed leukocytes because urine sediment DNA contains a high proportion of leukocyte-derived DNA.

The present invention overcomes limitations in the prior art by providing new methods for detecting the susceptibility to, predisposition for, presence of, and/or risk of developing or suffering from bladder cancer in a subject. The present invention is based, in part, on the identification that certain genes (e.g., DBC1, MYO3A, SOX11, NPTX2, NKX6-2, A2BP1, PENK and/or CA10) may be highly methylated in bladder tumors and can be detected in DNA from urine sediment to detect a bladder cancer. In one aspect, the methylation of one, two, three, four, five, six or all of the promoter or exon region of DBC1, MYO3A, SOX11, NPTX2, NKX6-2, A2BP1, PENK and/or CA10 may be evaluated from DNA in a urine sample to detect a cancer, such as a bladder cancer.

Early detection of cancer can result in improved clinical outcomes. Early and non invasive detection methods for bladder cancer screening and diagnosis of recurrence can be useful, e.g., in a high-risk population. As the bladder is the exclusive reserve organ for urine, urine sediments can provide a source of detection of exfoliated bladder tumor cells (Gazdar and Czerniak, 2001). In various embodiments, the methods of the present invention may be used in combination with one or more additional invasive (e.g., biopsy) or non-invasive test (e.g., cytology, FISH analysis and detection of mutations or microsatellite analysis in urine). A variety of non-invasive tests are known in the art and may be used with the present invention (see, e.g., Lotan and Roehrborn, 2003; van Rhijn et al., 2005; Hajdinjak, 2008).

DNA hypermethylation occurs at a high frequency in both, non-muscle invasive and invasive bladder cancers. As shown in the below examples, starting from an unbiased DNA methylation analysis screen, a panel of the least number of biomarkers that has high sensitivity and specificity was identified using a simple algorithm for detection of bladder cancer. With a sensitivity of about 85% and a specificity of about 95%, the positive predictive value (PPV) of various tests as disclosed herein would be about 52% based on an about 5.9% of prevalence in a high risk population that had history of smoking or symptoms of hematuria and dysuria (Grossman et al., 2005). This is about 1.2 to 8.7 times superior to what can be achieved by PSA testing (PPV=30-43%), mammography (PPV=9-19%) or fecal occult blood screening (PPV=6-11%) (Hoffman et al., 2002; Catalona et al., 1991; Richie et al., 1993; Brawer et al., 2000; Brown et al., 1995; Kerlikowske et al., 1993; Venkatesan et al., 2009; Mandel et al., 2000).

The panel of genes found by MCAM and validation by bisulfite pyrosequencing was methylated in 62-92% of 26 tested primary bladder tumors and most of bladder cancer cell lines analyzed. These are higher methylation frequencies than genes previously tested for bladder cancer detection (Hogue et al., 2006); without wishing to be bound by any theory, this may at least partially explain various improvements in the performance of the assay using, e.g., only 5 biomarkers (e.g., [MYO3A, SOX11, CA10, DBC1, and NKX6.2] or [MYO3A, CA10, DBC1, PENK, and NKX6.2]). As shown in the below examples, a evaluating the methylation status of five genes, MYO3A+CA10+NKX6-2+DBC1+SOX11 or MYO3A+CA10+NKX6-2+DBC1+PENK, showed higher sensitivity with preserved specificity compared to a previous report (Hogue et al., 2006) of a panel of 9 genes. In some embodiments, one or more of the biomarkers may be evaluated in combination with evaluation of promoter CpG islands, and it is anticipated that sequences such as exonic CpG islands may provide additional sensitivity for cancer detection.

The DNA methylation biomarker panels of the present invention may help the early detection with significant accuracy. In addition to screening, the non invasive early detection methods as provided herein may reduce the cystoscopy frequency. In some embodiments, the biomarkers may be detected or measured to evaluate the progression or determine the aggressiveness, metastatic potential, chemotherapeutic sensitivity, or prognosis of a cancer. In some embodiments, the methylation biomarkers may be used to evaluate or predict the responsiveness of a cancer to a therapy, such as a chemotherapy or surgery, in a subject. Kits for detecting methylation in the genes as described herein are also provided.

I. DEFINITIONS

"Attached" or "immobilized" as used herein to refer to a nucleic acid probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. $N^6$-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al. (2005); Soutschek et al. (2004); and U.S. Patent Publication No. 20050107325, which are incorporated herein by reference. Modified nucleotides and nucleic acids may also include locked nucleic acids (LNA), as described in U.S. Patent Publication No. 2002/0115080, U.S. Pat. No. 6,268,490, and U.S. Pat. No. 6,770,748, which are incorporated herein by reference. LNA nucleotides include a modified extra methylene "bridge" connecting the 2' oxygen and 4' carbon of the ribose ring. The bridge "locks" the ribose in the 3'-endo (North) conformation, which is often found in the A-form of DNA or RNA. LNA nucleotides can be mixed with DNA or RNA bases in the oligonucleotide whenever desired. Such oligomers are commercially available from companies including Exiqon (Vedbaek, Denmark). Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

"Substantially complementary" used herein may mean that a first sequence is at least 60%, 65%, 70%, 75%, 80%, 85%, 90%, or 95% identical to the complement of a second sequence over a region of 8, 9, 10, 11, 12, 13, 14, 15, 16, 17, 18, 19, 20, 21, 22, 23, 24, or more nucleotides, or that the two sequences hybridize under stringent hybridization conditions.

"Stringent hybridization conditions" used herein may mean conditions under which a first nucleic acid sequence will hybridize to a second nucleic acid sequence, such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

II. BLADDER CANCER

Certain aspects of the present invention are directed towards methods and/or kits for detecting the presence of, or an increased risk of, a bladder cancer in a subject. In other embodiments, it is anticipated that detection of methylation of biomarkers, e.g., in DNA from a urine sample, may be used to detect the presence of or an increased risk of other cancers, such as a prostate cancer, a testicular cancer, or a renal cancer. In some embodiments, the bladder cancer may be a cancer which has originated in the bladder or a metastatic cancer which is present in or adjacent to the bladder. Various types of bladder cancer may be detected or evaluated based on detection of methylation in a group of biomarkers as described herein. For example, the bladder cancer may have originated from one or more cells lining the bladder, e.g., transitional cells. The bladder cancer may comprise a papillary or a non-papillary tumor.

In some embodiments, DNA from or derived from a urine sample from a subject is analyzed to determine the presence or absence of methylation in a group of genes as described herein. Nonetheless, other biological samples may be used for this purpose, such as a biological sample comprising bladder cells, bladder cancer cells, bladder tissue, blood, serum, plasma, or a bladder tissue biopsy The biological sample may in some embodiments be derived or obtained from a urine sample.

III. DETECTION OF METHYLATION

In one aspect, the present invention is based on the relationship between a cancer such as a bladder cancer and methylation or hypermethylation in one, two, three, four, five, six, seven, or all of DBC1 (Gene ID: 1620, "deleted in bladder cancer 1"), MYO3A (Gene ID: 53904, "myosin MA"), SOX11 (Gene ID: 6664, "SRY (sex determining region Y)-box 11"), NPTX2 (Gene ID: 4885, "neuronal pentraxin II"), NKX6-2 (Gene ID: 84504, "NK6 homeobox 2"), A2BP1 (Gene ID: ID: 54715, "RNA binding protein, fox-1 homolog (C. elegans) 1" or "RBFOX1"), PENK (Gene ID: 5179, "proenkephalin") and/or CA10 (Gene ID: 56934, "carbonic anhydrase X"). Methylation typically occurs in a CpG containing nucleic acid. The CpG containing nucleic acid may be present in, e.g., in a CpG island, a CpG doublet, a promoter, an intron, or an exon. The CpG island may begin upstream a promoter and extend downstream into the transcribed region. The CpG containing nucleic acid is typically a DNA. However, the methylation of a gene may involve the analysis of a sample containing, e.g., DNA, DNA and RNA, messenger RNA, a single stranded or double stranded DNA or RNA, or a DNA-RNA hybrid.

Many of the methods for detecting the presence, absence, or amount of methylation involve exposing genomic DNA to bisulfite. Exposure of DNA, such as genomic DNA, to bisulfite can result in methylated cytosine in a CpG to remain without changes, while unmethylated cytosines are changed to uracil. Many methods for detecting methylation of a gene involve the treatment of DNA with bisulfite, and subsequent analysis of the resulting nucleotide. Other methods which may be used to detect methylation of a gene include, e.g., Combined Bisulfite Restriction Analysis (COBRA) and methylated DNA immunoprecipitation (MeDIP) (Xiong et al., 1997; Weber et al., 2005; Keshet et al., 2006). In some embodiments direct sequencing may be used to detect methylation (Frommer et al., 1992); however, some of the more recently developed methods have improved efficiency, as compared to direct sequencing.

A variety of methods for detecting the presence, absence, or amount of methylation in a gene are known in the art and may be used to evaluate the methylation status of one or more genes as described herein. For example, methylation specific PCR (MSP), real-time methylation specific PCR, methylation-sensitive single-strand conformation analysis (MS-SSCA), quantitative methylation specific PCR (QMSP), PCR using a methylated DNA-specific binding protein, high resolution melting analysis (HRM), methylation-sensitive single-nucleotide primer extension (MS-SnuPE), base-specific cleavage/MALDI-TOF, PCR, real-time PCR, Combined Bisulfite Restriction Analysis (COBRA), methylated DNA immunoprecipitation (MeDIP), a microarray-based method, pyrosequencing, or bisulfite sequencing may be used to detect and/or quantify methylation in a gene. Various methods for detecting methylation are disclosed, e.g., in US 2011/0046009, US 2010/0304992, U.S. Pat. No. 5,786,146; Fraga, 2002; El-Maarri, 2003; Laird, 2003; and Callinan, 2006, which are incorporated herein by reference in their entirety.

A. Methylation Specific PCR (MSP)

Methylation specific PCR typically utilizes bisulfite treatment of a nucleic acid to detect methylation. For a base sequence modified by bisulfite treatment, PCR primers corresponding to regions in which a 5'-CpG-3' base sequence is present may be constructed. For example, two kinds of primers corresponding to the methylated case and the unmethylated case may be generated. More specifically, primer pairs may thus be designed to be "methylated-specific" by including sequences complementing only unconverted 5-methylcytosines, or, on the converse, "unmethylated-specific", complementing thymines converted from unmethylated cytosines. Methylation is determined by the ability of the specific primer to achieve amplification. When genomic DNA is modified with bisulfite and then subjected to PCR using the two kinds of primers, if DNA is methylated, then a PCR product can be made from the DNA from a primer corresponding to the methylated base sequence. In contrast, if that region of the gene is unmethylated, a PCR product can be made from the DNA based on a primer corresponding to the unmethylated base sequence. The methylation of DNA can be qualitatively analyzed, e.g., using agarose gel electrophoresis.

In some embodiments, placing the CpG pair at the 3'-end of a primer may improve the sensitivity. The initial report using MSP described sufficient sensitivity to detect methylation of 0.1% of alleles. In general, MSP and its related protocols are considered to be the most sensitive when interrogating the methylation status at a specific locus.

B. Real-Time Methylation-Specific PCR

Real-time methylation-specific PCR generally involves a real-time measurement method, such as real-time PCR, modified from methylation-specific PCR. The method may involve treating genomic DNA with bisulfite, and utilizing metylated-specific and unmethylated-specific PCR primers in combination with real-time PCR. The method may involve performing detection using a TAQMAN probe complementary to the amplified base sequence, or detection using SYBER green. Generally, real-time methylation-specific PCR can quantitatively analyze DNA. A standard curve may be prepared using an in vitro methylated DNA sample, and for standardization, a gene having no 5'-CpG-3' sequence in the base sequence may be amplified as a negative control; in this way the degree of methylation of a gene may be calculated.

The MethyLight method is an example of a method that is based on MSP, but can provide a quantitative analysis using real-time PCR (Eads et al., 2000). Methylated-specific primers are typically used, and a methylated-specific fluorescence reporter probe may also be used to anneal to the amplified region. Alternately, the primers or probe can be designed without methylation specificity, e.g., if discrimination is desired between the CpG pairs within the involved sequences. Quantitation can be calculated in comparison to a methylated reference DNA. This protocol may be modified to increase the specificity of the PCR for successfully bisulfite-converted DNA (ConLight-MSP) by using an additional probe to bisulfite-unconverted DNA to quantify a non-specific amplification (Rand et al., 2002).

Melting-curve analysis (Mc-MSP) may be used to quantify the amount of methylation in a DNA, and generally involves the evaluation of MSP-amplified DNA (Akey et al., 2002). This method generally involves amplifying bisulfite-converted DNA with both methylated-specific and unmethylated-specific primers, and determining the quantitative ratio of the two products by comparing the differential peaks generated in a melting-curve analysis. Some Mc-MSP methods may use both real-time quantification and melting analysis, which may be particularly useful, e.g., for sensitive detection of low-level methylation (Kristensen et al., 2008).

C. Pyrosequencing

Pyrosequencing may be used to detect the presence, absence, or amount of methylation of a gene. Pyrosequencing may be used to analyze bisulfite-treated DNA without the need for methylation-specific PCR (Colella et al., 2003; Tost et al., 2003). Following PCR amplification of the region of interest, pyrosequencing may be used to determine the bisulfite-converted sequence of specific CpG sites in the region. The ratio of C-to-T at individual sites can be determined quantitatively based on the amount of C and T incorporation during the sequence extension. Pyrosequencing may be particularly effective for high-throughput screening methods. In some embodiments, allele-specific primers may be used that incorporate single-nucleotide polymorphisms into the sequence of the sequencing primer (Wong et al., 2006).

D. Base-Specific Cleavage/MALDI-TOF

Base-specific cleavage/MALDI-TOF may be used to detect methylation of a gene (Ehrich et al. 2005). This method typically involves using in vitro transcription of the region of interest into RNA (e.g., by adding an RNA polymerase promoter site to the PCR primer in the initial amplification), and then cleavage of the RNA transcript at base-specific sites with RNase A. Since RNase A can cleave RNA specifically at cytosine and uracil ribonucleotides, base-specificity is achieved by adding incorporating cleavage-resistant dTTP when cytosine-specific (C-specific) cleavage is desired, and incorporating dCTP when uracil-specific (U-specific) cleavage is desired. The cleaved fragments can then be analyzed by MALDI-TOF. Bisulfite treatment can result in either introduction/removal of cleavage sites by C-to-U conversions or shift in fragment mass by G-to-A conversions in the amplified reverse strand. C-specific cleavage can cut specifically at the methylated CpG sites. By analyzing the sizes of the resulting fragments, it is possible to determine the specific pattern of DNA methylation of CpG sites within the region, rather than determining the extent of methylation of the region as a whole.

E. Methylation-Sensitive Single-Strand Conformation Analysis (MS-SSCA)

Methylation-sensitive single-strand conformation analysis (MS-SSCA) may be used to detect methylation in a gene. This method is based on the single-strand conformation polymorphism analysis (SSCA) method, which has been used for single-nucleotide polymorphism (SNP) analysis (Bianco et al., 1999). SSCA can differentiate between single-stranded DNA fragments of identical size but distinct sequence based on differential migration in non-denaturating electrophoresis. In MS-SSCA, this approach can be used to distinguish between bisulfite-treated, PCR-amplified regions containing the CpG sites of interest. Bisulfite treatment of DNA can make C-to-T conversions in most regions, which can result in high sensitivity. MS-SSCA can provide semi-quantitative analysis of the degree of DNA methylation based on the ratio of band intensities. This method may be used to evaluate most or all CpG sites in a DNA region of interest.

F. High Resolution Melting Analysis (HRM)

High-resolution melting analysis (HRM) is a real-time PCR-based technique which may be used to detect methylation methylation, e.g., by differentiating converted from unconverted bisulfite-treated DNA (Wojdacz and Dobrovic, 2007). PCR amplicons can be analyzed directly by temperature ramping and resulting liberation of an intercalating fluorescent dye during melting. The degree of methylation, as represented by the C-to-T content in the amplicon, can be used to determine the rapidity of melting and consequent release of the dye. This method can allow for detecting methylation in a gene in a single-tube assay.

G. Methylation-Sensitive Single-Nucleotide Primer Extension (MS-SnuPE)

Methylation-sensitive single-nucleotide primer extension (MS-SnuPE) may be used to detect methylation of a gene (Gonzalgo and Jones, 1997). DNA is bisulfite-converted, and bisulfite-specific primers are annealed to the sequence up to the base pair immediately before the CpG of interest. The primer is allowed to extend one base pair into the C (or T) using DNA polymerase terminating dideoxynucleotides, and the ratio of C to T is determined quantitatively. The C:T ratio may be determined by a variety of techniques including, e.g., radioactive ddNTPs incorporation, fluorescence-based methods, pyrosequencing, matrix-assisted laser desorption ionization/time-of-flight (MALDI-TOF) mass spectrometry, or ion pair reverse-phase high-performance liquid chromatography (IP-RP-HPLC) has also been used to distinguish primer extension products (Uhlmann et al., 2002; Matin et al., 2002).

H. Detection of Differential Methylation-Methylation Sensitive Restriction Endonuclease Detection of methylation in a gene can be accomplished, in some embodiments, by contacting a nucleic acid sample with a methylation sensitive restriction endonuclease that cleaves only unmethylated CpG sites under conditions and for a time to allow cleavage of unmethylated nucleic acid. In a separate reaction, the sample may be further contacted with an isoschizomer of the methylation sensitive restriction endonuclease that cleaves both methylated and unmethylated CpG-sites under conditions and for a time to allow cleavage of methylated nucleic acid. Specific primers may be added to the nucleic acid sample under conditions and for a time to allow nucleic acid amplification to occur. The presence of amplified product in the sample digested with methylation sensitive restriction endonuclease but absence of an amplified product in sample digested with an isoschizomer of the methylation sensitive restriction enzyme endonuclease that cleaves both methylated and unmethylated CpG-sites can indicate that methylation has occurred at the nucleic acid region being assayed. Lack of amplified product in the sample digested with methylation sensitive restriction endonuclease together with lack of an amplified product in the sample digested with an isoschizomer of the methylation sensitive restriction enzyme endonuclease that cleaves both methylated and unmethylated CpG-sites can indicate that methylation has not occurred at the nucleic acid region being assayed.

As used herein, a "methylation sensitive restriction endonuclease" is a restriction endonuclease that includes CG as part of its recognition site and has altered activity when the C is methylated as compared to when the C is not methylated (e.g., Sma I). Non-limiting examples of methylation sensitive restriction endonucleases include MspI, HpaII, BssHII, BstUI, SacII and EagI and NotI. An "isoschizomer" of a methylation sensitive restriction endonuclease is a restriction endonuclease that recognizes the same recognition site as a methylation sensitive restriction endonuclease but cleaves both methylated CGs and unmethylated CGs, such as for example, MspI.

I. Microarray and DNA Chip-Based Methods

Microarray-based or DNA Chip-based methods may be used to detect methylation, e.g., in bisulfite-treated DNA (Adorjan et al., 2002). An oligonucleotide microarray or DNA chip may be produced using oligonucleotide pairs targeting CpG sites of interest, e.g., with one or more primer complementary to a methylated sequence, and another primer complimentary to a C-to-U-converted unmethylated sequence. The oligonucleotides may be bisulfite-specific to prevent binding to any DNA which has been incompletely converted by bisulfite. Microarray-based methods include, e.g., the Illumina Methylation Assay. In some embodiments, a microarray or DNA chip may be configured to detect methylation in one, two, three, four, five, six, seven, or all of DBC1 (Gene ID: 1620, "deleted in bladder cancer 1"), MYO3A (Gene ID: 53904, "myosin IIIA"), SOX11 (Gene ID: 6664, "SRY (sex determining region Y)-box 11"), NPTX2 (Gene ID: 4885, "neuronal pentraxin II"), NKX6-2 (Gene ID: 84504, "NK6 homeobox 2"), A2BP1 (Gene ID: 54715, "RNA binding protein, fox-1 homolog (C. elegans) 1" or "RBFOX1"), PENK (Gene ID: 5179, "proenkephalin") and/or CA10 (Gene ID: 56934, "carbonic anhydrase X").

IV. KITS

The technology herein includes kits for evaluating presence, absence, or amount of methylation in DBC1, MYO3A, SOX11, NPTX2, NKX6-2, A2BP1, PENK and/or CA10 in a sample. A "kit" refers to a combination of physical elements. For example, a kit may include, for example, one or more components such as probes, including without limitation specific primers, antibodies, a protein-capture agent, a reagent, an instruction sheet, and other elements useful to practice the technology described herein. The kits may include one or more primers, such as primers for PCR, to detect methylation of one or more of the genes as described herein. These physical elements can be arranged in any way suitable for carrying out the invention.

Kits for analyzing methylation of one or more genes may include, for example, a set of oligonucleotide probes for detecting methylation in DBC1, MYO3A, SOX11, NPTX2, NKX6-2, A2BP1, PENK and/or CA10. The probes can be provided on a solid support, as in an array (e.g., a microarray), or in separate containers. The kits can include a set of oligonucleotide primers useful for amplifying a set of genes described herein, such as to perform PCR analysis. Kits can include further buffers, enzymes, labeling compounds, and the like. Any of the compositions described herein may be comprised in a kit. The kit may further include water and hybridization buffer to facilitate hybridization of the two nucleic acid strands.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a single vial. The kits of the present invention also will typically include a means for containing the nucleic acids, and any other reagent containers in close confinement for commercial sale. Such containers may include injection or blow-molded plastic containers into which the desired vials are retained.

A kit will also include instructions for employing the kit components as well the use of any other reagent not included in the kit. Instructions may include variations that can be implemented. It is contemplated that such reagents are embodiments of kits of the invention. Such kits, however, are not limited to the particular items identified above and may include any reagent used for the manipulation or characterization of the methylation of a gene.

V. BIOCHIPS

A biochip is also provided. The biochip may comprise a solid substrate comprising an attached nucleic acid sequence that is capable of hybridizing to a methylated gene as described herein. "Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder. The probes may be attached to the biochip in a wide variety of ways, as will be appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TEFLON J, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linkers. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

VI. PERSONALIZING A THERAPY FOR THE TREATMENT OF BLADDER CANCER

In some aspects, detecting the presence, absence, or amount of methylation of one or more genes as described herein may be used to predicting the prognosis in a human subject with bladder cancer. In some embodiments, detecting methylation of one or more genes may be used to personalize a therapy or more effectively select a therapy for a human subject with bladder cancer. Detecting methylation of the one or more genes may be used, in some embodiments, to determine if or how a patient is responding to a therapy to treat a bladder cancer. In various embodiments, the presence, absence, or amount of methylation of the one or more genes can indicate which therapy will yield more or less favorable clinical results.

The bladder cancer therapy may include a surgery, an immunotherapy, a radiotherapy, or a chemotherapy. The surgery may involve removing a tumor without removing the rest of the bladder. In some instances, a chemotherapy or immunotherapy may be directly administered into the bladder. For more aggressive or advanced bladder cancers, a surgery may be performed to remove the entire bladder (radical cystectomy), or a surgery may be performed to remove only part of the bladder, which may be followed by radiation and chemotherapy. A chemotherapy may be administered to shrink the tumor before surgery. The therapy may involve the combination of a chemotherapy and a radiation therapy, e.g., in patients who choose not to have surgery or who cannot have surgery).

A chemotherapy may be given as a single drug or in different combinations of drugs. Chemotherapies for the treatment of a bladder cancer include, e.g., carboplatin, cisplatin, cyclophosphamide, docetaxel, doxorubicin, gemcitabine, ifosfamide, methotrexate, paclitaxel, mitomycin-C, thiotepa, and vinblastine. The combination of gemcitabine and cisplatin or MVAC (methotrexate, vinblastine, doxorubicin, and cisplatin). Paclitaxel and carboplatin may also be administered in combination. A Foley catheter may be used to deliver the medication into the bladder. Alternately, chemotherapy is usually given by vein (intravenously).

Bladder cancers may also be treated by administration of an immunotherapy to the subject. An immunotherapy for a bladder cancer may be performed using the Bacille Calmette-Guerin vaccine (commonly known as BCG), e.g., administered through a Foley catheter directly into the bladder. Interferon may be administered, e.g., subsequent to BCG, as an immunotherapy.

Surgeries which may be performed to treat a cancer include transurethral resection of the bladder (TURB) or bladder removal. These surgical procedures are typically performed under general or spinal anesthesia. A cutting instrument may be inserted through the urethra to remove the bladder tumor in TURB. Bladder removal (radical cystectomy) may be performed. Partial bladder removal may be performed in some patients. A surgery may be followed by radiation therapy and chemotherapy to help decrease the probability of the cancer returning. Radical cystectomy in men may involve removing the bladder, prostate, and seminal vesicles. In women, the urethra, uterus, and the front wall of the vagina may be removed along with the bladder. The pelvic lymph nodes may also be removed during the surgery. A urinary diversion surgery (a surgical procedure to create an alternate method for urine storage) may be performed with radical cystectomy. Two common types of urinary diversion are an ileal conduit and a continent urinary reservoir. An orthotopic neobladder surgery may be performed in patients undergoing cystectomy. In this surgery, a segment of bowel is folded over to make a pouch (a neobladder, which means "new bladder"). Then it is attached to the urethra where the urine normally empties from the bladder.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Samples Analyzed

Six (6) human bladder cancer cell lines (UM-UC-2 (T24), UM-UC-3, UM-UC-6, UM-UC-9, UM-UC-13 and UM-UC-14) and 26 fresh cystectomy specimens (11 cases of papillary, 13 cases of non-papillary and 2 cases of squamous cell carcinoma) from patients who underwent surgery at The University of Texas MD Anderson Cancer Center were evaluated. Normal urothelial cells were prepared from ureters of nephrectomy specimens and used as a control. First-voided urine was collected from 128 bladder cancer patients with cystoscopically evident bladder cancer before they underwent surgery at The University of Texas MD Anderson Cancer Center. Among 128 cases, primary cancers were 88 cases and recurrent cancers were 40 cases. There were no age, gender, ethnic, or cancer stage restrictions on recruitment. Age-matched controls (n=110) were recruited in medicine and urology clinics at The University of Texas Southwestern Medical Center (Dallas, Tex.). Controls consisted of 71 patients with benign urologic disorder without cystoscopically visible bladder cancer and 39 unaffected healthy individuals. The majority of controls visited the hospital for annual medical check-up. Fifty ml of the urine was centrifuged for 15 minutes at 200 g, and the resulting pelleted material was washed twice with PBS and stored at −70° C. until study. DNA from urine sediments was extracted by QIAAMP DNA Mini Kit (Qiagen, Germantown, Md.). All samples were collected from consenting patients according to institutional guidelines at The University of Texas MD Anderson Cancer Center and The University of Texas Southwestern Medical Center.

CpG Methylation Analysis by Bisulfite Pyrosequencing and qMSP

Figure 4:
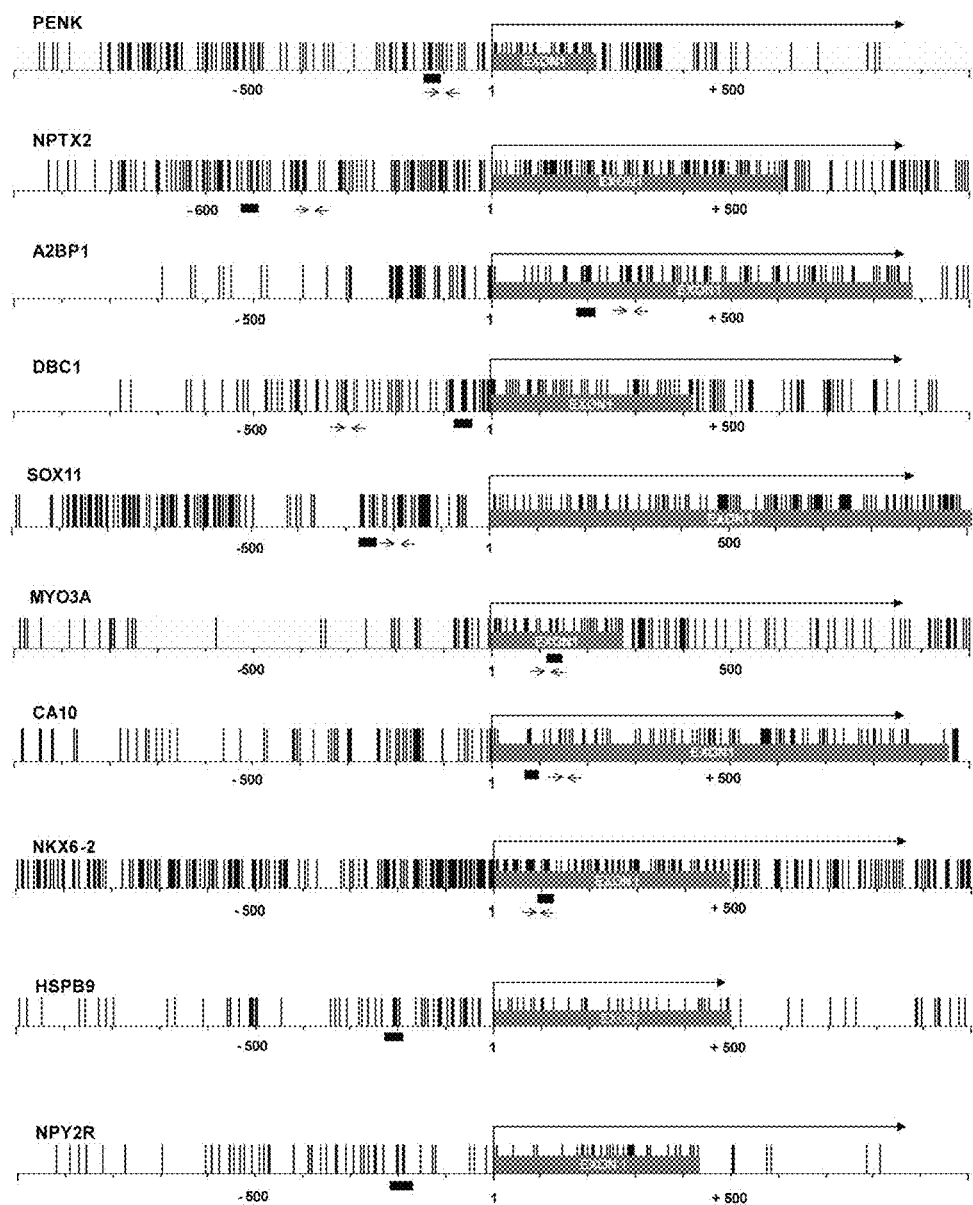
FIG. 4: CpG map and location of bisulfite pyrosequencing sites and qMSP primers for the methylation biomarkers studied. Each vertical black bar is a CpG site. Black rectangles below indicate CpG sites analyzed by bisulfite pyrosequencing. Arrow lines (→ and ←) indicate the location of qMSP primers.

Bisulfite conversion of extracted DNA was performed by EpiTect Bisulfite Kits (Qiagen). Ten genes (A2BP1, NPTX2, SOX11, PENK, NKX6-2, DBC1, MYO3A, HSPB9, NPY2R and CA10) were selected and studied by bisulfite pyrosequencing to analyze the quantitative methylation status (FIG. 4 and Table 2) in 6 bladder cancer cell lines and 26 primary bladder tumors. DNA methylation was analyzed for normal leukocytes and a mixture of normal bladder DNA from 3 persons (2 males and 1 female) as a control. Bisulfite-treated DNA was amplified by hot start and a two-step PCR to reduce the contamination in products due to the amplification of unexpected primer binding sites. A universal primer sequence tag was added to the reverse primer in the nested PCR step, as previously described. For pyrosequencing, biotin-labeled DNA strands were prepared and analyzed by PSQ HS 96 Pyrosequencing System (Biotage AB, Uppsala, Sweden). M.SssI methylase (New England Biolabs, Beverly, Mass.)-treated normal leukocytes DNA was used as a positive control for methylation studies. Bisulfite pyrosequencing in primary bladder tumors was conducted twice and averaged. To call a cancer as methylation positive, it was required that its methylation status was at least 10% higher than that seen in a mixture of normal bladder DNA.

TABLE 1

Demographic and clinical characteristics of the bladder cancer patients (n = 128)

| | Characteristics | No. of subjects (%) |
|---|---|---|
| Histological cell | Transitional cell carcinoma (TCC) | 110 (86.0) |
| | Squamous cell carcinoma | 8 (6.3) |
| | Mixed | 5 (3.9) |
| | Adenocarcinoma | 2 (1.6) |
| | Small-cell carcinoma | 2 (1.6) |
| | Pleomorphic sarcomatoid | 1 (0.8) |
| Race | Caucasian | 114 (89.1) |
| | African American | 10 (7.8) |
| | Hispanic | 2 (1.6) |
| | Latin American | 2 (1.6) |
| Age | <41 | 9 (7.0) |
| | 41-50 | 4 (3.1) |
| | 51-60 | 20 (15.6) |
| | 61-70 | 40 (31.3) |
| | 71-80 | 42 (32.8) |
| | >80 | 13 (10.2) |
| Gender | Male | 101 (78.9) |
| | Female | 27 (21.1) |
| Grade | 1 | 7 (5.5) |
| | 2 | 13 (10.2) |
| | 3 | 108 (84.4) |
| Stage | Ta | 30 (23.4) |
| | Tis | 5 (3.9) |
| | T1 | 23 (18.0) |
| | T2 | 62 (48.4) |
| | T3 | 6 (4.7) |
| | T4 | 2 (1.6) |

TABLE 2

Primers for bisulfite pyrosequencing.

| Primers Names | Sequences (5' to 3') | SEQ ID NO | Analyzed CpGs (from TSS) | Analyzed sequences | Annealing Temp. (° C.) for 1st PCR |
|---|---|---|---|---|---|
| MYO3A-106F1 | TTTTAGAGGGGAGGGTAGGGGTAGT | 1 | +122, | GGGYGGGT | 59 |
| MYO3A-106R1-89R2 | TCCACTCCATTAACCCAAATCAA | 2 | +125, | YGAAGGTY | |
| MYO3A-89F2 | GGGGTAGTAGAGTAGGGGAAGAAT | 3 | +131 | G | |
| MYO3A-89R2U | U-TCCACTCCATTAACCCAAATCAA | 4 | | (SEQ ID | |
| MYO3A-89S | AGAATTGGGTAGTTTGTAGA | 5 | | NO: 79) | |
| | | | | | |
| SOX11-154F1 | AGTTGGGGGAGTGATGTTATTTA | 6 | -272, | GAGYGYGY | 60 |
| SOX11-154R1 | AACAACCCCAAACCCCTCTCT | 7 | -270, | GYG | |
| SOX11-99F2 | GGGGGAGTGATGTTATTTATATGAT | 8 | -268, | (SEQ ID | |
| SOX11-99R2 | ACCCCCAACTCTCCCAAAC | 9 | -266 | NO: 80) | |
| SOX11-99R2U | U-CCCCCAACTCTCCCAAAC | 10 | | | |
| SOX11-99S | GAGATTTTAATTTTTGTAGAAG | 11 | | | |
| | | | | | |
| DBC1-118F1 | TGGAGAATGGAGAGGGAAGTTT | 12 | -63, | TGYGTYGY | 58 |
| DBC1-118R1 | CCCCTCCCCCATTCATTTT | 13 | -56, | G | |
| DBC1-118R1U | U-CCCCTCCCCCATTCATTTT | 14 | -53 | (SEQ ID | |
| DBC1-118S | TGGAGAGGGAAGTTTAAG | 15 | | NO: 81) | |
| | | | | | |
| A2BP1-124F1-62F2 | GGGGATTGGAAAGGAGGTGA | 16 | +190, | TYGYGTTYG | 60 |
| A2BP1-124R1 | CTCCCCCCCTCCTACAAA | 17 | +188, | (SEQ ID | |
| A2BP1-62R2 | CCCCAACCCCCTTCCTAA | 18 | +184 | NO: 82) | |
| A2BP1-62R2U | U-CCCCAACCCCCTTCCTAA | 19 | | | |
| A2BP1-62S | AAGGAGGTGATTTTTAAATT | 20 | | | |
| | | | | | |
| NPTX2-171F1-63F2 | GGGTTTTGAAGAGAAGGTTTA | 21 | -513, | YGTTTGTYG | 58 |
| NPTX2-171R1 | TACCCCTTTCTCAAAATAACTTCTAAC | 22 | -506, | YG | |
| NPTX2-63R2 | TCCAACCCCCACTACCATC | 23 | -504 | (SEQ ID | |
| NPTX2-63R2U | U-TCCAACCCCCACTACCATC | 24 | | NO: 83) | |
| NPTX2-63S | GGTTTTGAAGAGAAGGTTTA | 25 | | | |
| | | | | | |
| PENK-146F1-112R2 | GGAAAGAGTAGGGTGTTTAGGT | 26 | -149, | TTYGYGTTG | 60 |
| PENK-146R1 | CCCCCAAAAATACTCCTTTCT | 27 | -147, | GGGGYG | |
| PENK-112R2 | CCCCACCCACAACTTTTAA | 28 | -138 | (SEQ ID | |
| PENK-112R2U | U-CCCCACCCACAACTTTTAA | 29 | | NO: 84) | |
| PENK-112S | GAGTAGGGTGTTTTAGGTAGT | 30 | | | |
| | | | | | |
| CA10-114F1-94F2 | TAGGAGAGGGAAATAAAGATTTTTGTAGTTGTAT | 74 | +67, +73, | TTYGATAGY GGYG | 58 |
| CA10-114R1 | CTATTTTCCTAAACTCCCCAAAACC | 75 | +76 | (SEQ ID | |
| CA10-94R2 | AAACCCCAATTACCTAACTTCCA | 76 | | NO: 85) | |
| CA10-94R2U | U-AACCCCCAATTACCTAACTTCCA | 77 | | | |
| CA10-94S | GTAGTTGTATTGAGGAAAAT | 78 | | | |

TABLE 2-continued

Primers for bisulfite pyrosequencing.

| Primers Names | Sequences (5' to 3') | SEQ ID NO | Analyzed CpGs (from TSS) | Analyzed sequences | Annealing Temp. (° C.) for 1st PCR |
|---|---|---|---|---|---|
| NKX6-2 122F1-94F2 | GAGGGGTTAGGATGGGAGTT | 59 | +98, +102, +106, +108 | AATYGTTYG GGYGYG (SEQ ID NO: 86) | 59 |
| NKX6-2 122R1 | CTCTTCATCTCCACCATATTATACA | 60 | | | |
| NKX6-2 94R2 | CCACCAACCAAACACTACTCAA | 61 | | | |
| NKX6-2 94R2U | U-CCACCAACCAAACACTACTCAA | 62 | | | |
| NKX6-2 94S | GGAGGAGTTTATGGATATT | 63 | | | |
| HSPB9-114F1 | TATTAAAGAAGGTGGGGAAGGG | 64 | -212, -218, -216 | GTTGYGGG YGYG (SEQ ID NO: 87) | 60 |
| HSPB9-114R1-83R2 | TCAACCACCCCCATCTTACC | 65 | | | |
| HSPB9-83F2 | GGTAGGAGTTTGGGAGGAGAGTA | 66 | | | |
| HSPB9-83R2U | U-TCAACCACCCCCATCTTACC | 67 | | | |
| HSPB9-83S | GAGTTTGGGAGGAGAGTA | 68 | | | |
| NPY2R-97F1 | GATTTGGTGAAGTAGGTTTTAAGTTTAGG | 69 | -209, -206 | TTTGTTTTY GTYG (SEQ ID NO: 88) | 58 |
| NPY2R-97R1-89R2 | TCCACCAATCTCTCCCTTTACTCT | 70 | | | |
| NPY2R-89F2 | GAAGTAGGTTTTAAGTTTAGGAGGTTTG | 71 | | | |
| NPY2R-89R2U | U-TCCACCAATCTCTCCCTTTACTCT | 72 | | | |
| NPY2R-89S | TAGGTTTTAAGTTTAGGAGG | 73 | | | |

Biotin labeled universal primer sequence (5'-biotin-GGGACACCGCTGATCGTTTA (SEQ ID NO: 31)) was added to the reverse primer in the second PCR step.

For qMSP, 8 genes were selected that had hypermethylation in bladder cancer and low levels of methylation in normal leukocytes. All primers were designed to have the same annealing temperature. Quantity of human DNA in urine was determined after bisulfite conversion by C-LESS DNA (chr20:19, 199,387-19, 199,455, UCSC Blat 2006 Mar. version), a unique sequence that does not contain cytosines (Weisenberger et al., 2008). Table 3 lists primers and TAQ-MAN probes (Applied Biosystems, Foster City, Calif.) for mC-LESS and the eight genes examined. For quality control, we adjusted diluted bisufite treated DNA to 100 µA throughout. We used the same volume (3 µl) of bisulfate treated DNA as template for every qMSP (total reaction volume, 20 µl). Each qMSP reaction batch was checked with positive (M SssI methylase treated DNA) and negative (normal leukocyte DNA) controls, and multiple blanks with no DNA. Each plate was amplified with mC-LESS (internal control) and the tested genes together to avoid inter-assay variation. We also used as validation criteria an intra-assay variation of $\Delta Ct<1$ at a duplicated sample and $r^2 \geq 0.99$ for at least 4 relevant Ct points. Normal leukocyte DNA was methylated in vitro with twice excess M. SssI methylase and 5-fold serial dilutions (100-0.032 ng) of this DNA were used to construct a calibration curve. When we compared the Ct of mC-LESS with those of other test genes, the correlation was $R^2 > 0.99$. All qMSP reactions were done in duplicate in a blinded manner and averaged. All samples were within the assay's range of sensitivity and reproducibility based on amplification of internal control (threshold cycle [Ct] value for mC-LESS of <40).

TABLE 3

Primers and probes for quantitative methylation specific real time PCR

| Primers Name | Sequences (5' to 3') | SEQ ID NO: | Annealing Temp. (° C.) |
|---|---|---|---|
| mC-LESS 69F | TTGTATGTATGTGAGTGTGGGAGA | 32 | 60 |
| mC-LESS 69R | TTTCTTCCACCCCTTCTCTTC | 33 | |
| mC-LESS probe | 6FAM-CTCCCCCTCTAACTCTAT-MGBNFQ | 34 | |
| MYO3A 62F | TCGGCGGGAGGATTTGAT | 35 | 60 |
| MYO3A 62R | CCCGCGAACCGAAATAAAA | 36 | |
| MYO3A probe | 6FAM-TGGGTTAATCGAGTCGAA-MGBNFQ | 37 | |
| CA10 60F | TTCGGCGTTTTGGACGTATT | 38 | 60 |
| CA10 60R | AATCCGCGCGCAACCTA | 39 | |
| CA10 probe | 6FAM-TCGGAATTCGGTTGAGAGG-MGBNFQ | 40 | |

TABLE 3-continued

Primers and probes for quantitative methylation specific real time PCR

| Primers Name | Sequences (5' to 3') | SEQ ID NO: | Annealing Temp. (° C.) |
|---|---|---|---|
| SOX11 81F | GGTAGGAGTTACGAGTCGGAGAGA | 41 | 60 |
| SOX11 81R | ACTACGATCGCGACAAAAAAAAC | 42 | |
| SOX11 probe | 6FAM-TCGGGTTGTTTCGATCG-MGBNFQ | 43 | |
| PENK 69F | CGCGTTATTTCGGGAATCG | 44 | 60 |
| PENK 69R | TCCCGACCGACAACTTTTAAATAAA | 45 | |
| PENK probe | 6FAM-AGGCGATTTGAGTCGTT-MGBNFQ | 46 | |
| NKX6-2 63F | GGCGGCGTTTATGGATATTAAT | 47 | 60 |
| NKX6-2 63R | GCGACCAACGAAACACTACTCA | 48 | |
| NKX6-2 probe | 6FAM-TTCGGGCGCGTTC-MGBNFQ | 49 | |
| DBC1-76F | CGTGTAGGGTGTTGTGTTTATGC | 50 | 60 |
| DBC1-76R | AACACCAAAATTCCGAATTTACG | 51 | |
| DBC1 Probe | 6FAM-ATTTAAAGGGATCGCGTATAC-MGBNFQ | 52 | |
| NPTX2-71F | TGAGGGCGGCGGTAAAC | 53 | 60 |
| NPTX2-71R | CCCGATACCCCTTTCTCAAAA | 54 | |
| NPTX2 Probe | 6FAM-TGTCGCGTTAGAAGTT-MGBNFQ | 55 | |
| A2BP1-90F | GGTTTCGTTCGTCGTTCGTTAT | 56 | 60 |
| A2BP1-90R | CCTCCTCCAACCAAAATCGA | 57 | |
| A2BP1 Probe | 6FAM-TTCGCGTTGTTTGGAGAA-MGBNFQ | 58 | |

6FAM, fluorescent dye 6-carboxyfluorescein; MGBNFQ, minor groove binder/non-fluorescent quencher.

Statistical Analysis

The relative level of methylated DNA for each gene in each sample was determined as a ΔCt of qMSP-amplified gene to mC-LESS (internal control). The samples were categorized as unmethylated or methylated based on the criterion values and coordinates of the receiver operating characteristics (ROC) curve of the assay.

The predictive accuracy of biomarkers was evaluated by calculating the area under the ROC curve (AUC) and Akaike information criterion (AIC) (Li and Nyhold, 2001). The ROC curve of both specificity and sensitivity of single or combined biomarkers sets consisting of up to 8 methylation biomarkers was constructed.

To discover potentially predictive relationship, the model was optimized using a training set and tested on the test set. The 128 urine samples from bladder tumor (T) patients and 110 urine samples from control (N) subjects were randomly divided into the training set containing two third (T=84 and N=73) of samples and the rest of samples form a test set (T=34 and N=37). Statistical analyses were performed using GraphPad Prism 4 software (GraphPad Software Inc., San Diego, Calif.) and SPSS statistical software V11.0 (SPSS Inc., Chicago, Ill.). All p values were two-sided and $P<0.05$ was considered statistically significant. When multiple tests were performed, Bonferroni corrections were applied to the p-values.

Example 2

Methylation of Genes for Detecting Bladder Cancer in a Subject

Bisulfite pyrosequencing results of 10 selected genes in 6 bladder cancer cell lines and 26 primary bladder tumors are shown in FIG. 1. Eight genes (A2BP1, NPTX2, SOX11, PENK, NKX6-2, DBC1, MYO3A and CA10) were highly methylated in bladder tumors and had very low levels of methylation in normal leukocytes. Their methylation frequencies in 26 primary bladder cancer were 62%, 88%, 77%, 92%, 69%, 69%, 65% and 85%, respectively. HSPB9 was highly methylated in both bladder tumors and normal leukocytes. NPY2R showed lower methylation frequency (54%) than the other genes in bladder tumors.

To apply this gene panel to early detection, DNA methylation was first analyzed by bisulfite pyrosequencing in urine sediments for two genes, SOX11 and HSPB9 as examples. SOX11 showed increased methylation in urine from bladder cancer patients compared to control but the differences were small, in part due to the relatively high background of pyrosequencing (5%). HSPB9 was highly methylated in the urine sediment of controls, and similarly methylated (though more variable) in the urine sediment of patients (FIGS. 5A-B). These results are consistent with the fact that urine sediment DNA contains a high proportion of leukocyte-derived DNA (even in patients with cancer) and that detection of cancer would require more sensitive and clear cutoff point methods to detect a low frequency of tumor-derived DNA. The qMSP method was applied to overcome these problems and the 8 genes (DBC1, MYO3A, SOX11, NPTX2, NKX6-2, A2BP1, PENK and CA10) which had low levels of methylation in normal leukocytes were analyzed.

Figure 2:
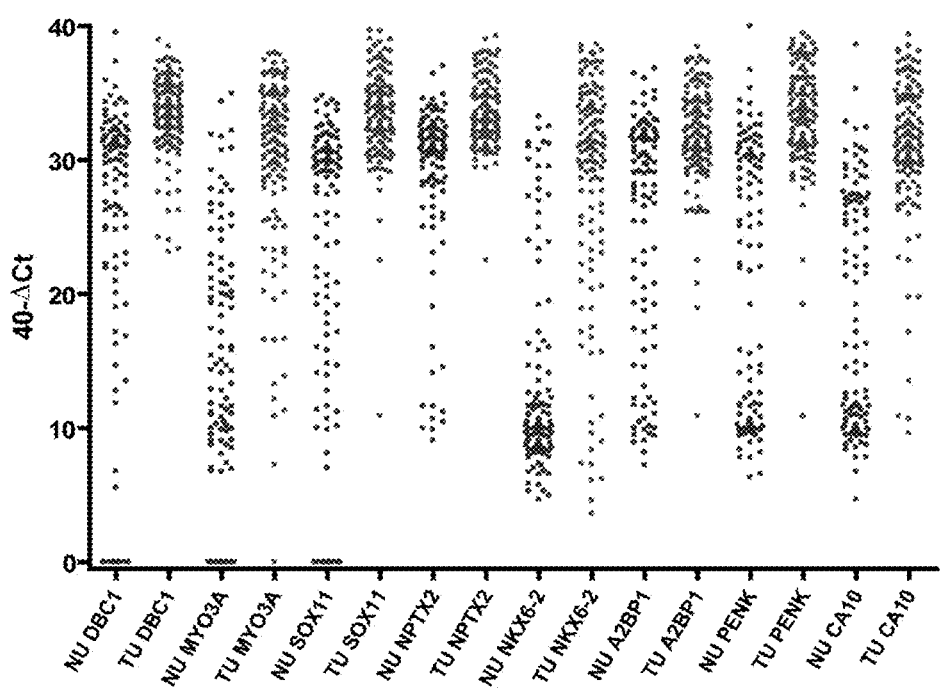
FIG. 2: Graph of qMSP results of each gene in urine sediments of bladder cancer patients (n=128) and controls (n=110). The relative level of methylated DNA is depicted as 40-dCt[Ct of specific gene−Ct of mC-LESS (internal control)]. A higher 40-dCt represents more methylation of the target biomarker. All 8 genes show significantly more methylation in tumor cases than controls (P<0.0001).

Overall, we studied urine sediments from 128 bladder cancer patients (median age 69) and 110 control subjects (median age 67) (Table 1 and Table 4). The bladder cancer patients consisted of 58 cases of non-muscle invasive tumors (30 cases of pTa, 5 cases of Tis and 23 cases of T1) and 70 cases of muscle invasive tumors (62 cases of T2, 6 cases of T3 and 2 cases of T4). Most (87%) of them were of TCC type. Control subjects consisted of 71 cases of benign urologic symptoms, 39 normal controls including 5 healthy volunteers Control subjects consisted of 90 cases of urologic symptoms without malignancy, 15 patients who had primary cancers at sites other than the bladder and 5 healthy volunteers (Table 4). The distribution of qMSP results of each gene in urine sediments is shown in FIG. 2. It All 8 genes showed substantially and significantly more methylation in tumor cases than controls (P<0.0001). Because qMSP is only semi-quantitative, cutoffs were established to call a sample methylated or unmethylated, and to use the information in a multi-gene predictive model. To do this, the samples were divided randomly into a training set (⅔) used to obtain a prediction model and a test set (⅓). The training set consisted of 73 cases (67%) of normal controls and 84 cases (67%) of tumor patients (61 T1 to T4 stages and 23 pTa & Tis stages). The test set contained the remaining samples. There were no significant differences between the training and test data sets with respect to any of the measured demographic and clinicopathologic characteristics. ROC curves and AIC analysis were established to evaluate the performance of individual markers, as well as marker combinations.

TABLE 4

Demographic and clinical characteristics of controls (n = 110)

| Characteristics | No. of subjects (%) |
| --- | --- |
| Type of controls | |
| Benign urologic disorders | 71 (64.5) |
| Stress incontinence | 8 (7.3) |
| Benign prostate hyperplasia | 17 (15.5) |
| Stricture | 2 (1.8) |
| Kidney stone | 6 (5.5) |
| Hematuria | 4 (3.6) |
| Cystitis | 3 (2.7) |
| Bladder stone | 2 (1.8) |
| Chronic prostatitis | 2 (1.8) |
| Other vague urologic symptoms without malignancy | 27 (24.5) |
| Non urologic controls | 39 (35.5) |
| Benign hypertension | 13 (11.8) |
| Diabetes type II | 4 (3.6) |
| Kyphosis | 2 (1.8) |
| Primary cancers at sites other than the bladder | 15 (13.6) |
| Healthy volunteers | 5 (4.5) |
| Race | |
| Caucasian | 81 (73.6) |
| African American | 13 (11.8) |
| Asian | 5 (4.5) |
| Hispanic | 2 (1.8) |
| Native American | 1 (0.9) |
| Unknown | 8 (7.3) |
| Age | |
| <41 | 2 (1.8) |
| 41-50 | 9 (8.2) |
| 51-60 | 18 (16.4) |
| 61-70 | 43 (39.1) |
| 71-80 | 27 (24.5) |
| >80 | 11 (10.0) |
| Gender | |
| Male | 63 (57.3) |
| Female | 46 (41.8) |

The power of each methylation marker was evaluated by calculating the area under curve (AUC) of receiver operating characteristic (ROC) using total data set of 128 tumors and 110 controls. A random marker unrelated to bladder cancer is expected to have an AUC value of 0.5. The AUC values for the eight methylation markers we selected in the order from high to low are MYO3A (AUC=0.841, P<0.0001), CA10 (AUC=0.835, P<0.0001), NKX6-2 (AUC=0.823, P<0.0001), PENK (AUC=0.802, P<0.0001), SOX11 (AUC=0.797, P<0.0001), DBC1 (AUC=0.774, P<0.0001), NPTX2 (AUC=0.747, P<0.0001) and A2BP1 (AUC=0.710, P<0.0001). We also performed a correlation analysis for all pairs of markers (Table 5). All pairs of methylation level of genes were correlated with statistical significance (P<0.0001).

TABLE 5

Spearman correlation of methylation level of each gene of DNA in urine sediments

| Biomarker | NPTX2 | A2BP1 | SOX11 | MYO3A | NKX6-2 | PENK | CA10 |
| --- | --- | --- | --- | --- | --- | --- | --- |
| DBC1 | 0.55 | 0.57 | 0.71 | 0.56 | 0.49 | 0.62 | 0.63 |
| NPTX2 | | 0.70 | 0.59 | 0.55 | 0.63 | 0.74 | 0.63 |
| A2BP1 | | | 0.59 | 0.56 | 0.52 | 0.71 | 0.64 |
| SOX11 | | | | 0.70 | 0.57 | 0.72 | 0.66 |
| MYO3A | | | | | 0.61 | 0.66 | 0.68 |
| NKX6-2 | | | | | | 0.64 | 0.60 |
| PENK | | | | | | | 0.71 |

Each gene methylation level was 40-dCt(qMSP) of the gene.
All correlations were statistically significant (P < 0.0001).

To develop a multi-gene predictive model, we used a combinatorial analysis of methylation of 8 biomarkers. In this analysis, a model including 4 genes, MYO3A+CA10+NKX6-2+DBC1 or MYO3A+CA10+NKX6-2+SOX11 yielded an AUC of 0.939 (95% CI=0.901 to 0.966, P<0.0001) for the set [tumor patients urine (TU)=128 and controls urine (NU)=110]. The models including 5 genes, MYO3A+CA10+NKX6-2+DBC1+SOX11 or MYO3A+CA10+NKX6-2+DBC1+PENK yielded the same AUC of 0.939 (95% CI=0.901 to 0.966, P<0.0001) (FIGS. 6A-B).

To estimate the performance of the assay with greater precision, we then used the combined dataset (TU=128 and NU=110). Based on the AUC of the combined dataset, the order of high to low ranked biomarkers is MYO3A (AUC=0.841), CA10 (AUC=0.835), NKX6-2 (AUC=0.823), PENK (AUC=0.802), SOX11 (AUC=0.797), DBC1 and an AUC of 0.933 (CI=0.894 to 0.962, P<0.0001). In the models of 4 gene panel (MYO3A+CA10+NKX6-2+DBC1 or MYO3A+CA10+NKX6-2+SOX11), if a urine sample has 3 or 4 genes methylation, the sensitivity was 81% (95% CI=73.4 to 87.6, P<0.0001) and specificity 97% (95% CI=92.2 to 99.4, P<0.0001). In the models of 5 gene panel (MYO3A+CA10+NKX6-2+DBC1+SOX11 or MYO3A+CA10+NKX6-2+DBC 1+PENK), if a sample has 3 or more than 3 gene methylation, the sensitivity was 85% (95% CI=77.8 to 90.8, P<0.0001) and specificity 95% (95% CI=88.5 to 98.0, P<0.0001). Panels of 4 or 5 selected methylation markers had the same AUC of 0.939 and showed the best accuracy of detection of bladder cancer in urine sediments (Table 6). Larger studies may be performed and may include, e.g., including a high risk population that has a history of heavy smoking or symptoms of hematuria, dysuria, urgent urination and/or frequent urinary tract infections.

TABLE 6

Diagnostic information of single or combined qMSP markers for detection of bladder cancer in urine sediments

| Biomarkers (No. of combined biomarkers) | Cutoff* | TP/FN | % Sensitivity | FP/TN | % Specificity | AUC |
|---|---|---|---|---|---|---|
| MYO3A | >0 | 99/29 | 77.3 | 100/10 | 90.9 | 0.841 |
| CA10 | >0 | 109/19 | 85.2 | 90/20 | 81.8 | 0.835 |
| NKX6-2 | >0 | 113/15 | 88.3 | 84/26 | 76.4 | 0.823 |
| PENK | >0 | 104/24 | 81.3 | 87/23 | 79.1 | 0.802 |
| SOX11 | >0 | 90/38 | 70.3 | 98/12 | 89.1 | 0.797 |
| DBC1 | >0 | 91/37 | 71.1 | 92/18 | 83.6 | 0.774 |
| NPTX2 | >0 | 97/31 | 75.8 | 81/29 | 73.6 | 0.747 |
| A2BP1 | >0 | 112/16 | 87.5 | 60/50 | 54.5 | 0.710 |
| MYO3A, NKX6-2 (2) | >1 | 92/36 | 71.9 | 107/3 | 97.3 | 0.914 |
| CA10, NKX6-2 (2) | >1 | 101/27 | 78.9 | 105/5 | 95.5 | 0.912 |
| MYO3A, CA10, NKX6-2 (3) | >1 | 110/18 | 85.9 | 102/8 | 92.7 | 0.933 |
| MYO3A, CA10, NKX6-2, PENK (4) | >2 | 104/24 | 81.3 | 107/3 | 97.3 | 0.936 |
| MYO3A, CA10, NKX6-2, SOX11 (4) | >2 | 104/24 | 81.3 | 107/3 | 97.3 | 0.939** |
| MYO3A, CA10, NKX6-2, DBC1 (4) | >2 | 104/24 | 81.3 | 107/3 | 97.3 | 0.939** |
| MYO3A, CA10, NKX6-2, NPTX2 (4) | >2 | 100/28 | 78.1 | 105/5 | 95.5 | 0.934 |
| MYO3A, CA10, NKX6-2, PENK, SOX11 (5) | >2 | 107/21 | 83.6 | 103/7 | 93.6 | 0.935 |
| MYO3A, CA10, NKX6-2, DBC1, SOX11 (5) | >2 | 109/19 | 85.2 | 104/6 | 94.5 | 0.939** |
| MYO3A, CA10, NKX6-2, DBC1, PENK (5) | >2 | 109/19 | 85.2 | 104/6 | 94.5 | 0.939** |
| MYO3A, CA10, NKX6-2, PENK, SOX11, DBC1 (6) | >3 | 105/23 | 82.0 | 108/2 | 98.2 | 0.937 |
| MYO3A, CA10, NKX6-2, PENK, SOX11, DBC1, NPTX2 (7) | >3 | 106/22 | 82.8 | 104/6 | 94.5 | 0.936 |
| MYO3A, CA10, NKX6-2, PENK, SOX11, DBC1, A2BP (7) | >4 | 105/23 | 82.0 | 108/2 | 98.2 | 0.930 |
| MYO3A, CA10, NKX6-2, PENK, SOX11, DBC1, A2BP, NPTX2 (8) | >4 | 105/23 | 82.0 | 104/6 | 94.5 | 0.928 |

*When the number of methylated biomarkers of the case passed cutoff value, we considered it as positive case.
**The best combinations of biomarker with the highest area under the ROC curve (AUC) value were shown by bold character (P < 0.0001). The other biomarker combinations did not improve the AUC.
Abbreviations:
TP, true positive;
FN, false negative;
FP, false positive;
TN, true negative.

Figure 3:
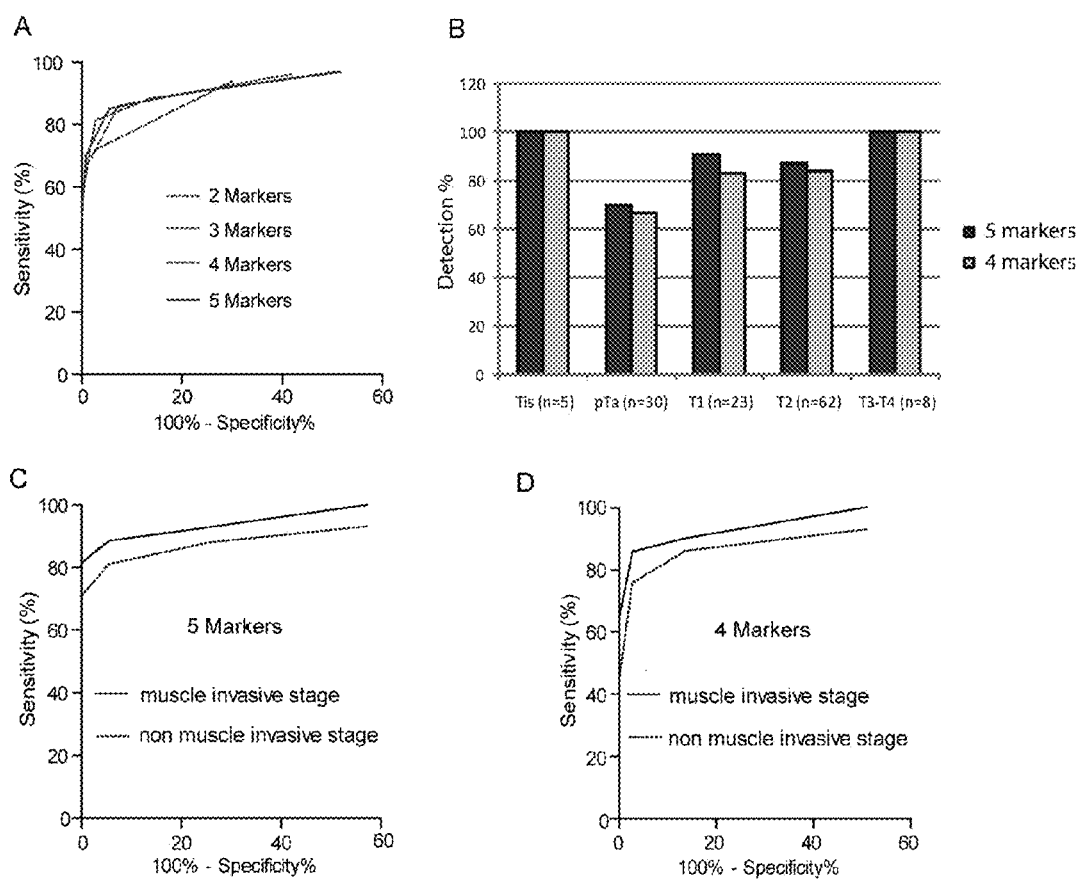
FIGS. 3A-D: Receiver operating characteristics (ROC) for bladder cancer detection of the combined dataset (TU=128 and NU=110).

(AUC=0.774), NPTX2 (AUC=0.747) and A2BP1 (AUC=0.710). The performances of single and combined qMSP markers for detection of bladder cancer in urine sediments are shown in Table 6. Comparison of ROC curve of the panel of combined markers was shown in FIG. 3A. In the panel of 3 genes (MYO3A+CA10+NKX6-2), if a urine sample has 2 or 3 genes methylation, the sensitivity was 86% (95% CI=78.7 to 91.4, P<0.0001) and specificity 93% (95% CI=86.2 to 96.8, P<0.0001) for detection of bladder tumors Analyzing by stage of bladder cancer using the 5-gene panel, detection rate based on 3 gene methylation or greater was 5 of 5 (100%) in Tis, 21 of 30 (70%) in pTa, 21 of 23 (91%) in T1, 54 of 62 (87%) in T2 and 8 of 8 (100%) in T3/T4 (FIG. 3B). Thus, cancer could be detected at a sensitivity of 81% and a specificity of 95% and an AUC of 0.911 (95% CI=0.857 to 0.949, P<0.0001) in non-muscle invasive stage bladder cancer (Tis-pTa-T1 stages) and a sensitivity of 90% and a specificity of 95% and an AUC of 0.962 (95% CI=0.923 to 0.985, P<0.0001) in invasive stage bladder cancer (T2-T3-T4 stages) (FIG. 3C). When classified by grade, detection rate by the 5-gene panel was 95 out of 111 (86%) in grade 3, 8 out of 13 (61%) in grade 2 and 1 out of 3 (33%) in grade 1. The 4-gene panel had a sensitivity/specificity of 76%/97% (AUC=0.913, P<0.0001) in Tis-pTa-T1 stages and 86%/97% (AUC=0.961, P<0.0001) in T2-T3-T4 stages. Analyzing the 2 control groups using the 5-gene panel, the benign urological group (n=71) had 3 false positive cases and the non urologic control group (n=39) had 3 false positive cases. There were no significant differences between the benign urological group and the normal control group. The detection rate of primary and recurrent cancers using the 5-gene panel was identical [75/88 (85%) and 34/40 (85%), respectively].

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,034,506
U.S. Pat. No. 5,235,033
U.S. Pat. No. 5,786,146
U.S. Pat. No. 6,268,490
U.S. Pat. No. 6,770,748
U.S. Patent Publn. 2002/0115080
U.S. Patent Publn. 2005/0182005
U.S. Patent Publn. 20050107325
U.S. Patent Publn. 2010/0304992
U.S. Patent Publn. 2011/0046009
Adorjan et al., *Nucleic Acids Res.*, 30(5):e21, 2002.
Akey et al., *Genomics*, 80(4):376-84, 2002.
Allard et al., *Br. J. Urol.*, 81:692-698, 1998.
Babjuk et al., *Eur. Urol.*, 54:303-314, 2008.
Bianco et al., *Hum. Mutat.*, 14(4):289-93, 1999.
Brawer et al., *J. Urol.*, 163:1476-1480, 2000.
Brown et al., *Am. J. Roentgenol.*, 165:1373-1377, 1995.
Callinan, *Hum. Mol. Genet.*, 15:R95-101, 2006.
Catalona et al., *N. Engl. J. Med.*, 324:1156-1161, 1991.
Colella et al., *BioTechniques*, 35(1):146-50, 2003.
Denzinger et al., *Urology*, 69:675-679, 2007.
Eads et al., *Nucleic Acids Res.*, 28(8):E32, 2000.
Ehrich et al. *Proc. Natl. Acad. Sci. USA*, 102(44):15785-90, 2005.
El-Maarri, *Adv. Exp. Med. Biol.*, 544:197-204, 2003.
Fraga, *BioTechniques*, 33(3):632, 634, 636-49, 2002.
Frommer et al. *Proc. Natl. Acad. Sci. USA*, 89(5):1827-31, 1992.
Gazdar and Czerniak, *J. Natl. Cancer Inst.*, 93:413-415, 2001.
Gonzalgo and Jones, *Nucleic Acids Res.*, 25(12):2529-31, 1997.
Grossman et al., *JAMA*, 293:810-816, 2005.
Hajdinjak, *Urol. Oncol.*, 26:646-651, 2008.
Hoffman et al., *BMC Fam. Pract.*, 3:19, 2002.
Hogue et al., *J. Natl. Cancer Inst.*, 98:996-1004, 2006.
Jemal et al., *Cancer J. Clin.*, 59:225-249, 2009.
Kerlikowske et al., *JAMA*, 270:2444-2450, 1993.
Keshet et al., *Nat. Genet.*, 38(2):149-53, 2006.
Kriegmair et al., *J. Urol.*, 155:105-109, 1996.
Kristensen et al., *Nucleic Acids Res.*, 36(7):e42, 2008.
Krutzfeldt et al. *J. Biol. Chem.*, 280:16635-41, 2005.
Kurth et al., *Eur. J. Cancer*, 31A:1840-1846, 1995.
Laird, *Nat. Rev. Cancer*, 3(4):253-66, 2003.
Li and Nyholt, *Genet. Epidemiol.*, 21(1):S272-S277, 2001.
Lotan and Roehrborn, *Urology*, 61:109-118, 2003.
Mandel et al., *N. Engl. J. Med.*, 343:1603-1607, 2000.
Matin et al., *Hum. Mutat.*, 20(4):305-11, 2002.
Papanicolaou and Marshall, *Science*, 101:519-520, 1945.
Rand et al., *Methods*, 27(2):114-20, 2002.
Richie et al., *Urology*, 42:365-374, 1993.
Soutschek et al., *Nature*, 432(7014):173-178, 2004.
Sylvester et al., *Eur. Urol.*, 49:466-477, 2006.
Tost et al. *Bio Techniques*, 35(1):152-6, 2003.
Uhlmann et al., *Electrophoresis*, 23(24):4072-9, 2002.
van Rhijn et al., *Eur. Urol.*, 47:736-748, 2005.
Venkatesan et al., *Radiology*, 250:648-657, 2009.
Weber et al., *Nat. Genet.*, 37(8):853-62, 2005.
Weisenberger et al., *Nucleic Acids Res.*, 36:4689-4698, 2008.
Wojdacz and Dobrovic, *Nucleic Acids Res.*, 35(6):e41, 2007.
Wong et al. *BioTechniques*, 41(6):734-9, 2006.
Xiong et al., *Nucleic Acids Res.*, 25(12):2532-2534, 1997.
Zaak et al., *Urology*, 57:690-694, 2001.
Feng et al., *Nat. Protoc.*, 5(7):1255-1264, 2010
Bock et al., *Nat. Biotechnol.* 28(10):1106-14. 2010
Smith et al., *Methods*. 48(3):226-32. 2009
Meissner et al., *Nucleic Acids Res.* 33(18):5868-77, 2005.
Li et al., *Nat. Biotechnol.* 27(9):858-63, 2009.
Diehl et al., *Nat. Methods*. 3(7):551-9, 2006.

What is claimed is:

1. A method of detecting the presence of, or an increased risk of, a bladder cancer in a subject, comprising the steps of:
   a) obtaining a biological sample from the subject comprising genomic DNA from the subject's bladder; and
   b) testing the genomic DNA using a DNA methylation assay by detecting or measuring the methylation status of at least three genes therein selected from the group of genes consisting of MYO3A, CA10, NKX6-2, SOX11, DBC1, NPTX2;
   c) determining the methylation status of the genes tested in step b) in a control sample comprising genomic DNA from normal bladder;
   d) comparing the methylation status of the genes tested in step b) to the methylation status of genes tested in step c) to determine whether the methylation status of the one or more of the genes determined in step b) is at least 10% higher than the methylation status determined for the genes tested in step c);
wherein if the methylation status of one or more of the genes tested in step b) is at least 10% higher than that of one or more genes tested in step c), then the subject has, or has an increased risk of having, bladder cancer as compared to subjects that do not exhibit such a methylation status in at least one of the genes so tested.

2. The method of claim 1, wherein said detecting or measuring comprises detecting or measuring methylation in MYO3A, CA10, and NKX6-2.

3. The method of claim 2, wherein said detecting or measuring further comprises detecting or measuring methylation in SOX11.

4. The method of claim 2, wherein said detecting or measuring further comprises detecting or measuring methylation in PENK.

5. The method of claim 1, wherein said detecting or measuring comprises detecting or measuring methylation in at least four of MYO3A, CA10, NKX6-2, SOX11, DBC1.

6. The method of claim 5, wherein said detecting or measuring comprises detecting or measuring methylation in MYO3A, CA10, NKX6-2, and DBC1.

7. The method of claim 6, wherein said detecting further comprises detecting or measuring methylation in SOX11.

8. The method of claim 6, wherein said detecting further comprises detecting or measuring methylation in PENK.

9. The method of claim 6, wherein said detecting or measuring comprises detecting or measuring methylation in MYO3A, SOX11, CA10, DBC1, PENK, and NKX6-2.

10. The method of claim 1, wherein the subject is a mammal.

11. The method of claim 10, wherein the mammal is a human.

12. The method of claim 1, wherein the biological sample comprises a urine sample, bladder cells, bladder tissue, or DNA from or derived from urine sediment.

13. The method of claim 12, wherein the biological sample comprises DNA from or derived from urine sediment.

14. The method of claim 1, wherein the bladder cancer comprises a papillary tumor.

15. The method of claim 1, wherein the bladder cancer comprises a non-papillary tumor.

16. The method of claim 1, wherein the method further comprises a method of measuring the aggressiveness of the bladder cancer.

17. The method of claim 1, wherein a personalized therapy is administered to the subject.

18. The method of claim 17, wherein the personalized therapy is a chemotherapeutic, an immunotherapy, a radiotherapy, or a surgery.

19. The method of claim 1, wherein the method further comprises monitoring the effectiveness of a therapy that is administered to the subject.

20. The method of claim 1, wherein the detecting or measuring comprises a method selected from the group consisting of methylation specific polymerase chain reaction (PCR-MSP), real-time methylation specific PCR, methylation-sensitive single-strand conformation analysis (MS-SSCA), quantitative methylation specific PCR (QMSP), polymerase chain reaction (PCR) using a methylated DNA-specific binding protein, high resolution melting analysis (HRM), methylation-sensitive single-nucleotide primer extension (MS-SnuPE), base-specific cleavage/matrix-assisted laser desorption/ionization-time of flight (MALDI-TOF), PCR, real-time PCR, Combined Bisulfite Restriction Analysis (COBRA), methylated DNA immunoprecipitation (MeDIP), a microarray-based method, pyrosequencing, and bisulfite sequencing.

21. The method of claim 20, wherein the detecting or measuring comprises methylation specific polymerase chain reaction (PCR), real-time methylation specific PCR, quantitative methylation specific PCR (QMSP), or bisulfite sequencing.

22. The method of claim 1, wherein the detecting or measuring comprises reduced representation bisulfite sequencing (RRBS), methyl beads, emulsion, amplification and magnetics (methyl-BEAMing), or fluorescence resonance energy transfer (FRET) technique for detection of DNA methylation.

* * * * *